(12) United States Patent
Thomas et al.

(10) Patent No.: US 11,944,405 B2
(45) Date of Patent: *Apr. 2, 2024

(54) PRESSURE-SENSING DEVICES

(71) Applicant: THERAPY HOLDINGS, INC., San Francisco, CA (US)

(72) Inventors: Jonathan Moulton Thomas, San Francisco, CA (US); Brian James Krieger, San Francisco, CA (US); Elizabeth Ann Miracle, San Francisco, CA (US); Grace Hina Lee, San Francisco, CA (US)

(73) Assignee: THERAPY HOLDINGS, INC., San Francisco, CA (US)

( * ) Notice: Subject to any disclaimer, the term of this patent is extended or adjusted under 35 U.S.C. 154(b) by 492 days.

This patent is subject to a terminal disclaimer.

(21) Appl. No.: 17/179,939

(22) Filed: Feb. 19, 2021

(65) Prior Publication Data

US 2021/0169325 A1 Jun. 10, 2021

Related U.S. Application Data

(63) Continuation of application No. 15/281,411, filed on Sep. 30, 2016, now Pat. No. 10,925,487.

(Continued)

(51) Int. Cl.
*A61B 5/00* (2006.01)
*A61B 5/11* (2006.01)
*A61B 5/22* (2006.01)

(52) U.S. Cl.
CPC .......... *A61B 5/0002* (2013.01); *A61B 5/1107* (2013.01); *A61B 5/227* (2013.01);
(Continued)

(58) Field of Classification Search
CPC ..... A61B 5/0002; A61B 5/1107; A61B 5/227; A61B 5/486; A61B 5/0247; A61B 5/164; A61B 2562/0247; A61B 2562/164
See application file for complete search history.

(56) References Cited

U.S. PATENT DOCUMENTS

| 4,989,615 A | 2/1991 | Hochberg |
| 5,267,988 A | 12/1993 | Farkas |

(Continued)

FOREIGN PATENT DOCUMENTS

| CN | 104434146 A | 3/2015 |
| WO | 2016042310 A1 | 3/2016 |

OTHER PUBLICATIONS

U.S. Appl. No. 15/281,411, filed Sep. 30, 2016, Thomas et al.

(Continued)

*Primary Examiner* — Devin B Henson
*Assistant Examiner* — Evelyn Grace Park
(74) *Attorney, Agent, or Firm* — RMCK Law Group PLC

(57) ABSTRACT

A pressure-sensing device includes a device frame, a flexible membrane, a pressure sensor, and device electronics. The device frame includes a base surface that rests on a supporting structure and a frame attachment region located opposite to the base surface such that the frame attachment region is raised from the supporting structure when the base surface is resting on the supporting structure. The device frame also includes a seating surface. The flexible membrane is attached to the frame attachment region such that the device frame and the flexible membrane enclose a pressure chamber. The seating surface extends outward around the flexible membrane and the flexible membrane protrudes above the seating surface. The pressure sensor is configured to generate a pressure signal. The device elec- (Continued)

tronics are configured to determine the pressure in the pressure chamber based on the pressure signal.

21 Claims, 25 Drawing Sheets

Related U.S. Application Data

(60) Provisional application No. 62/237,197, filed on Oct. 5, 2015.

(52) U.S. Cl.
CPC ............ *A61B 5/486* (2013.01); *A61B 5/4561* (2013.01); *A61B 5/6885* (2013.01); *A61B 2560/0257* (2013.01); *A61B 2560/0412* (2013.01); *A61B 2562/0247* (2013.01); *A61B 2562/164* (2013.01); *A61B 2562/168* (2013.01)

(56) References Cited

U.S. PATENT DOCUMENTS

| | | |
|---|---|---|
| 5,531,226 A | 7/1996 | Harris |
| 6,436,029 B1 | 8/2002 | Benderev |
| 7,338,417 B2 | 3/2008 | Kang |
| 7,473,214 B2 | 1/2009 | Stekhoven et al. |
| 2009/0156967 A1 | 6/2009 | Cohen |
| 2011/0098613 A1 | 4/2011 | Thomas et al. |
| 2015/0273270 A1 | 10/2015 | Brinkhaus et al. |
| 2015/0335851 A1 | 11/2015 | Cullen et al. |

OTHER PUBLICATIONS kGoal description published Jun. 23, 2014.
kGoal MediaKit LO3, published Jun. 17, 2014.
kGoal press release FINAL—a press release released on Jan. 26, 2015.
MINNA kGoalBooklet LO2, Jan. 30, 2015.

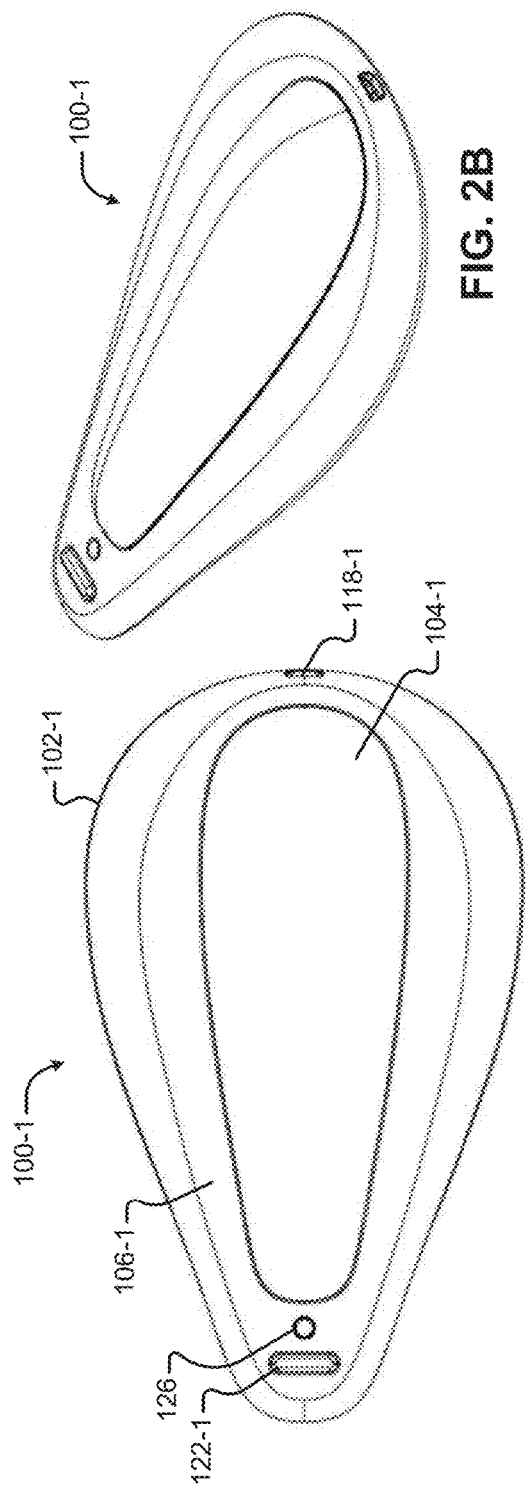
FIG. 2A
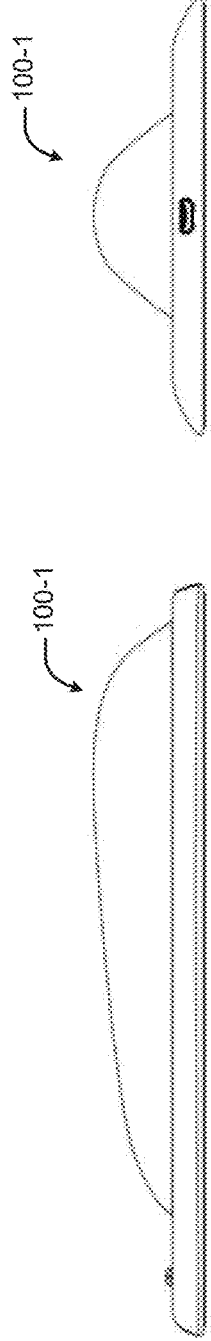
FIG. 2B
FIG. 2C
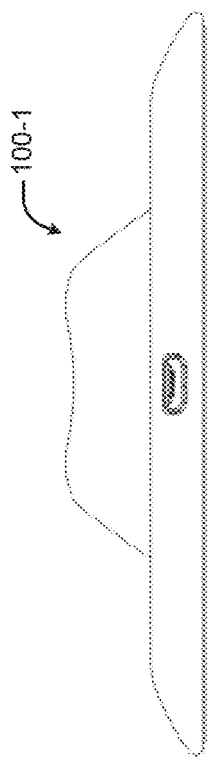
FIG. 2D
FIG. 2E

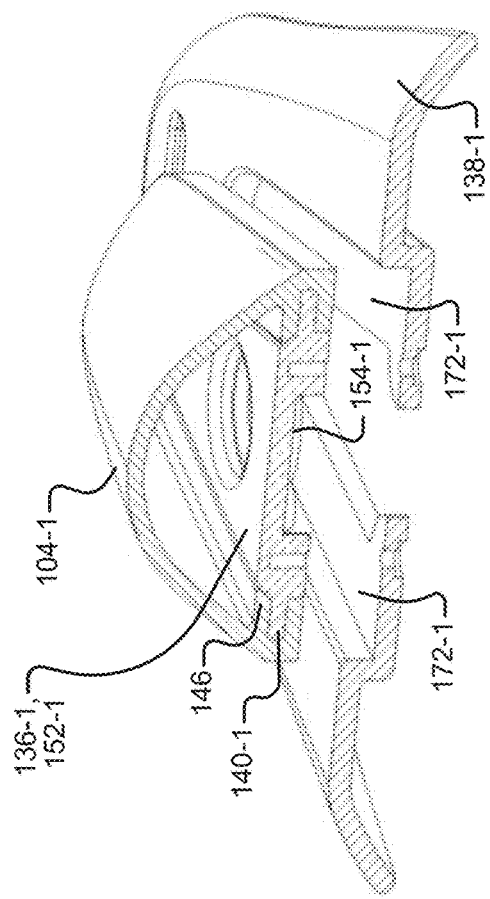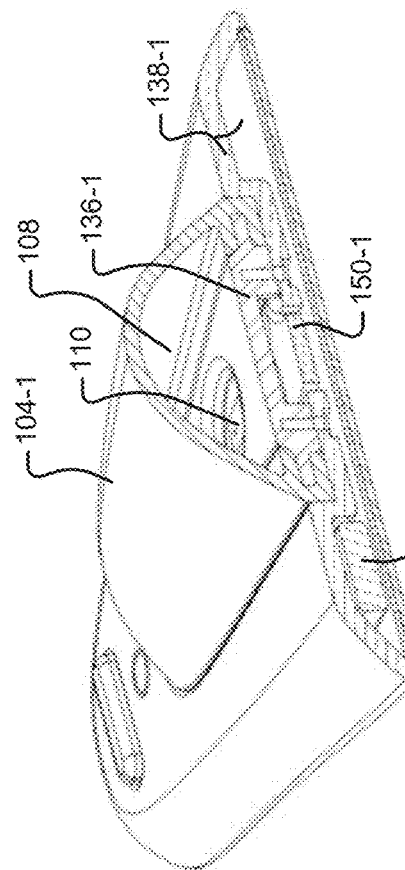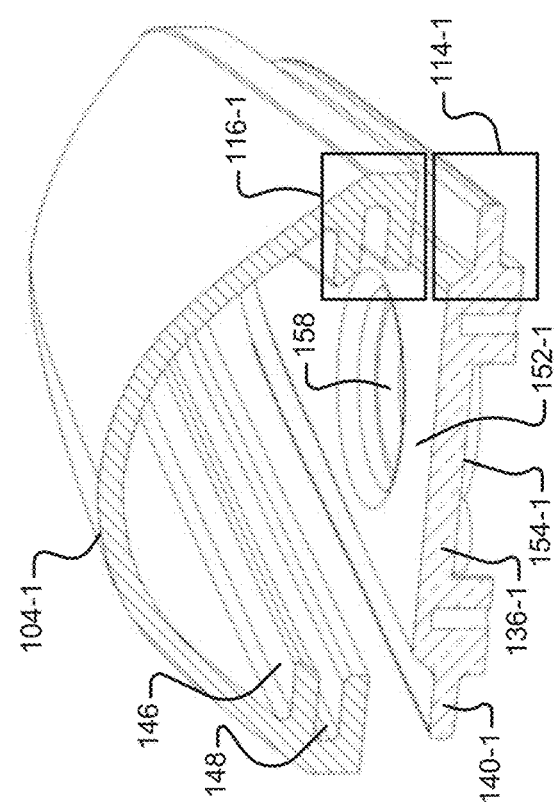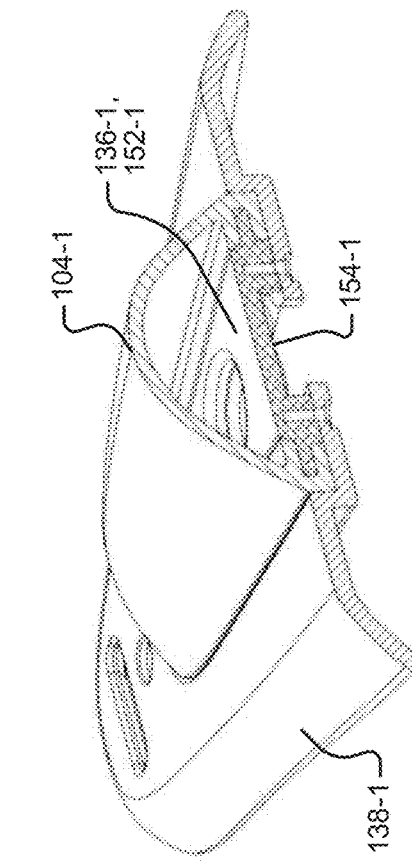
FIG. 7A
FIG. 7B
FIG. 7C
FIG. 7D

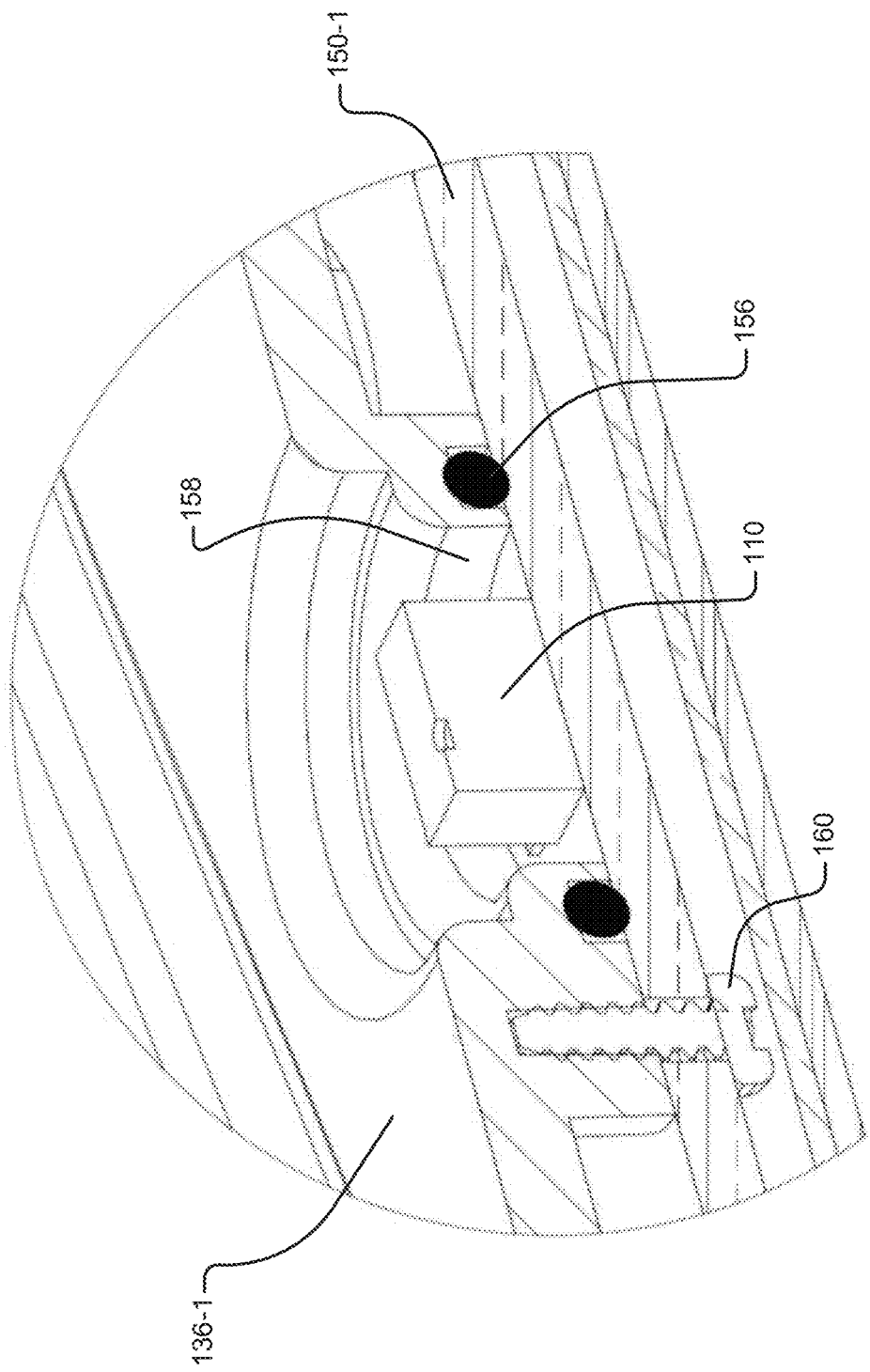

PRESSURE-SENSING DEVICES

CROSS-REFERENCE TO RELATED APPLICATIONS

This application is a continuation of U.S. patent application Ser. No. 15/281,411, filed Sep. 30, 2016, which U.S. patent application claims priority under 35 U.S.C. § 119(e) to U.S. Provisional Application 62/237,197, filed on Oct. 5, 2015, which are both hereby incorporated by reference in their entirety.

FIELD

The present disclosure relates to pressure-sensing devices.

BACKGROUND

The human body includes a network of muscles located at the base of the abdomen that may be referred to as the pelvic floor. The pelvic floor may include the Pubococcygeus, Illiococcgeus, Coccygeus, Bulbospongiosus, Ischiospongiosus, and Deep Transverse Perineii muscles. These muscles may perform important functions. For example, for both men and women, maintaining healthy pelvic floor muscles may help improve bladder and bowel control, reduce back pain, increase balance, and enhance sexual function. In some cases, these muscles may become weak, damaged, or ineffective, which may result in a variety of ailments. Regular exercise of these muscles may therefore be important to keeping them functioning properly. Pelvic floor muscle exercises (contraction and relaxation) are commonly referred to as Kegel exercises, or Kegels for short.

SUMMARY

In one aspect, the present disclosure is directed to a pressure-sensing device comprising a device frame, a flexible membrane, a pressure sensor, and device electronics. The device frame comprises a base surface configured to rest on an external supporting structure and a frame attachment region located opposite to the base surface such that the frame attachment region is raised from the external supporting structure when the base surface is resting on the external supporting structure. The device frame also comprises a seating surface. The flexible membrane includes a membrane attachment region attached to the frame attachment region. The device frame and the flexible membrane at least partially enclose a pressure chamber between the device frame and the flexible membrane. The seating surface extends outward around the flexible membrane and the flexible membrane protrudes above the seating surface. The pressure sensor is at least partially included within the pressure chamber. The pressure sensor is configured to generate a pressure signal indicating a pressure in the pressure chamber. The device electronics are in communication with the pressure sensor. The device electronics are configured to determine the pressure in the pressure chamber based on the pressure signal.

In another aspect, the present disclosure is directed to a pressure-sensing device comprising a device frame, a flexible membrane, a pressure sensor, and device electronics. The device frame comprises a base surface configured to rest on an external supporting structure and a frame attachment region located opposite to the base surface such that the frame attachment region is raised from the external supporting structure when the base surface is resting on the external supporting structure. The device frame includes a sidewall that extends from the base surface towards the frame attachment region. The flexible membrane includes a membrane attachment region attached to the frame attachment region. The device frame and the flexible membrane at least partially enclose a pressure chamber between the device frame and the flexible membrane. The pressure sensor is at least partially included within the pressure chamber. The pressure sensor is configured to generate a pressure signal indicating a pressure in the pressure chamber. The device electronics are in communication with the pressure sensor. The sidewall encircles the device electronics. The device electronics are configured to determine the pressure in the pressure chamber based on the pressure signal.

In yet another aspect, the present disclosure is directed to a pressure-sensing device comprising a device frame, a flexible membrane, a pressure sensor, and device electronics. The flexible membrane is attached to the device frame. The device frame and the flexible membrane at least partially enclose a pressure chamber between the device frame and the flexible membrane. The flexible membrane is configured to conform to a user's perineum region when the user sits on the flexible membrane. The pressure sensor is at least partially included within the pressure chamber. The pressure sensor is configured to generate a pressure signal indicating a pressure in the pressure chamber. The device electronics are in communication with the pressure sensor. The device electronics are configured to determine the pressure in the pressure chamber based on the pressure signal and detect a muscle contraction in the user's perineum region based on the determined pressure.

BRIEF DESCRIPTION OF THE DRAWINGS

The present disclosure will become more fully understood from the detailed description and the accompanying drawings.

FIGS. 1A-2E illustrate a first example pressure-sensing device.

FIGS. 4-15 illustrate example internal features of the first and second pressure-sensing devices.

In the drawings, reference numbers may be reused to identify similar and/or identical elements.

DETAILED DESCRIPTION

Figure 1A:
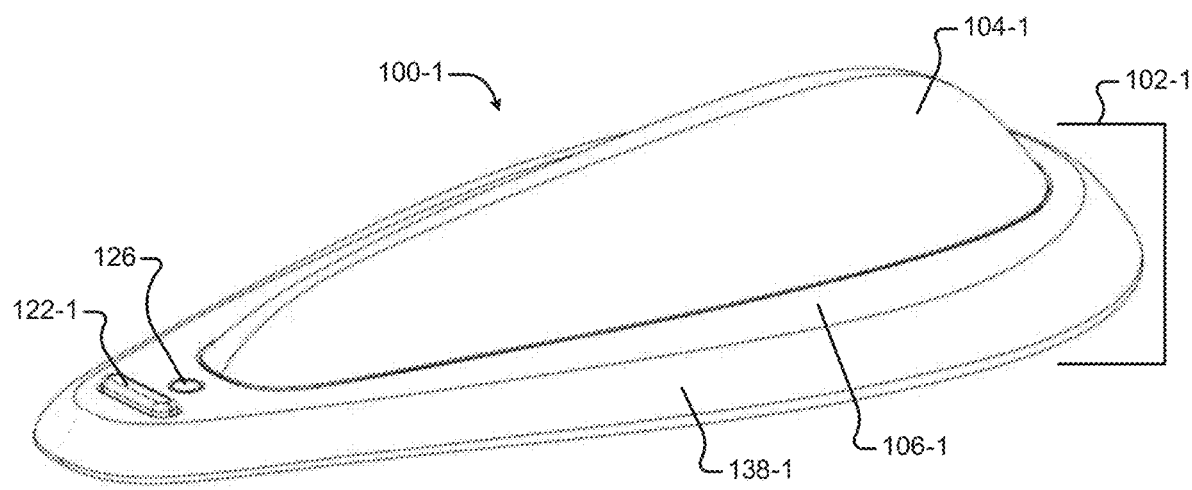

The present disclosure describes a variety of different pressure-sensing devices 100 (e.g., 100-1, 100-2 of FIGS. 1A-3B). The pressure-sensing devices 100 include a device frame 102 (e.g., 102-1, 102-2 of FIGS. 1A-3B) and a flexible membrane 104 (e.g., 104-1, 104-2 of FIGS. 1A-3B) that is attached to the device frame 102. The pressure-sensing devices 100 can be fabricated in different shapes and sizes. In some implementations, the pressure-sensing devices 100 can be fabricated with a device frame 102 (e.g., 102-1 of FIG. 1A) that protrudes out from the edges of where the flexible membrane 104 attaches to the device frame 102. In these implementations, the portion of the device frame 102 that extends outward around the flexible membrane 104 may provide a seating surface 106 (e.g., 106-1 of FIG. 1A and 106-4 of FIG. 19A) for stabilizing the pressure-sensing device 100 during use. In other implementations, the device frame 102 (e.g., 102-2 of FIG. 3A) may not extend outward as a seating surface around the flexible membrane 104. Instead, in these implementations, the sidewalls of the pressure-sensing device 100 may extend downward away from the region where the flexible membrane 104 attaches to the device frame 102. In still other implementations, the pressure-sensing devices 100 can be fabricated in other shapes (e.g., FIGS. 19C-19F).

Figure 16B:
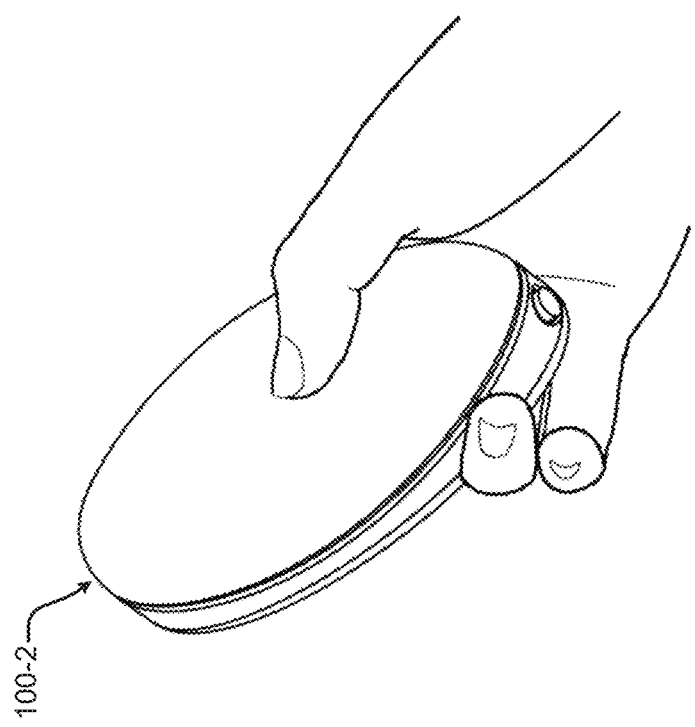
FIGS. 16A and 16B illustrate handheld implementations of the first and second pressure-sensing devices.
Figure 16A:
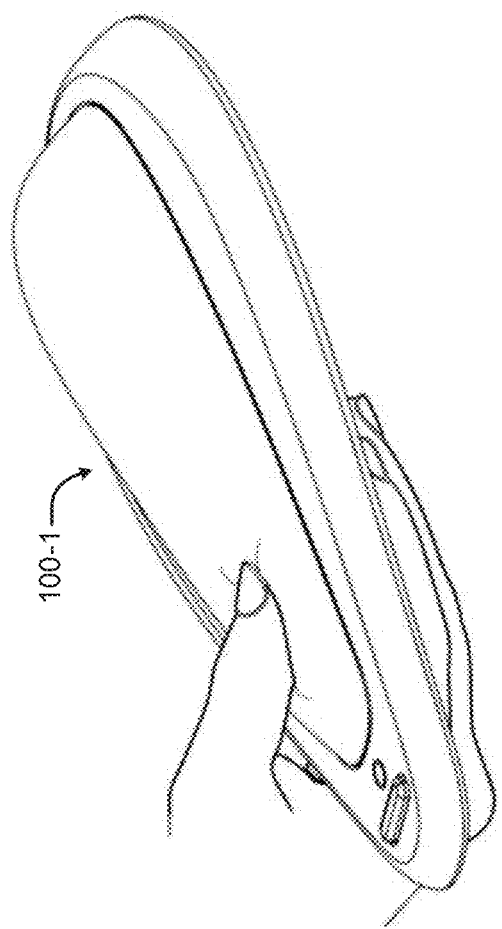

In implementations illustrated herein, the flexible membrane 104 can be fabricated as a single piece of material having a smooth surface (e.g., see FIGS. 16A and 16B). Although the flexible membrane 104 illustrated herein can be fabricated as a single piece of material having a smooth surface, some of the figures (e.g., FIG. 1A, 2B, 8B, 19A-19E) include visible lines on the surface of the flexible membrane 104. In these figures, the visible lines are meant to illustrate the contour of the flexible membrane 104, as opposed to a feature on the outer surface of the flexible membrane 104. Although the flexible membrane 104 is illustrated as a single piece of material herein, in other implementations, the flexible membrane may be fabricated from more than one piece of material.

The device frame 102 can refer to the rigid portion of the pressure-sensing device 100 that holds the flexible membrane 104 in position while the pressure-sensing device 100 is in use. The pressure-sensing device 100 may include a pressure chamber (e.g., 108 of FIG. 4) defined by the flexible membrane 104 and the device frame 102. The pressure-sensing device 100 includes a pressure sensor (e.g., 110 of FIG. 4) and device electronics for measuring pressure developed in the pressure chamber 108 as a result of deformation of the flexible membrane 104 during use. The pressure-sensing device 100 can also include user interface components (e.g., buttons and lights) along with wired and/or wireless communication and charging components. In some implementations, the pressure-sensing device 100 can communicate with a user computing device (e.g., 220 of FIG. 20) executing an application for interacting with the pressure-sensing device 100.

The pressure-sensing devices 100 can be used for monitoring various exercise activities. For example, the pressure-sensing devices 100 can be used for monitoring contractions of a user's pelvic floor muscles (e.g., in the user's perineum region). Example muscles that may be involved during use of the pressure-sensing devices 100 may include the Pubococcygeus, Illiococcgeus, Coccygeus, Bulbospongiosus, Ischiospongiosus and Deep Transverse Perineii muscles. Exercising these muscles may provide various health benefits, such as improved bladder control, reduction in back pain, increased balance, and a reduction in erectile dysfunction.

Some illustrated pressure-sensing devices 100 (e.g., 100-1, 100-2) have a dome shaped flexible membrane 104 (e.g., an elongated dome shape). The pressure-sensing devices 100 may be shaped such that, while a user is sitting on the device, the flexible membrane 104 makes contact with the user's body and/or clothes and conforms to their body. In one example, the elongated dome shape may conform to the perineum region of the user's body. The deformation shape of the flexible membrane 104 illustrated in FIG. 2E and FIG. 8B is for illustration purposes only. During actual use, muscle contractions may deform the flexible membrane 104 in a more evenly distributed manner. For example, when the user sits on the pressure-sensing device 100, the flexible membrane 104 may be significantly flattened as the air inside the pressure chamber 108 is compressed. From the compressed state, the flexible membrane movement may be subtle and may not be a point-deformation as shown in the figures, but may likely be a general downward pressure on much of the flexible membrane surface.

In examples where the pressure-sensing device 100 is used in the perineum region of the user, the elongated shape of the flexible membrane 104 may provide tolerance as to the exact position of the user. For example, the user may effectively use the pressure-sensing device 100 while positioned forward/rearward of the center of the dome. The pressure-sensing device 100 can be used in direct contact with a user's skin and/or a user's clothing. Since the pressure-sensing device 100 may be configured to measure small changes in pressure (e.g., small displacements of the flexible membrane 104), the pressure-sensing device 100 may measure small user movements, even through a user's clothing.

The size of the pressure chamber 108 (e.g., the dimensions of the flexible membrane 104) may be selected based on the expected size of the user. For example, different sizes of the pressure-sensing device 100 may be made for fitting different sized users (e.g., larger users may use larger devices). The size of the pressure chamber 108 may also be selected based on the expected change in pressure to be measured during use. In the case of a larger pressure chamber, a given displacement of the flexible membrane may lead to a smaller change in pressure, thereby being more difficult to detect. Accordingly, there may be a benefit to having a smaller pressure chamber that is compressed proportionally more during use, as compared to a larger pressure chamber. Having a rigid device frame 102 may increase the sensitivity of the pressure-sensing device 100 to small displacements of the flexible membrane 104. For example, for a given size pressure chamber, the sensitivity may be increased by having more of the pressure chamber 108 constrained by a rigid boundary that is not deformed during use. Although a rigid device frame 102 may be used in the illustrated pressure-sensing devices 100, in other implementations, some or all of the device frame may be fabricated from flexible components.

The device frame 102 has a base surface 112 (e.g., 112-1, 112-2 of FIG. 1B and FIG. 3B) that can be formed from the same material as the rest of the device frame 102, or from a different material (e.g., as an attached base pad). The base surface 112 may be configured to rest on an external supporting structure, such as a chair. The device frame 102 includes a frame attachment region 114 (e.g., 114-1, 114-2 of FIG. 7A and FIG. 8) which may refer to the area of the device frame 102 to which the flexible membrane 104 is attached. The frame attachment region 114 is located opposite to the base surface 112 such that the frame attachment region 114 is raised from the external supporting structure when the base surface 112 is resting on the external supporting structure.

The flexible membrane 104 may include a membrane attachment region 116 (e.g., 116-1, 116-2 of FIG. 7A and FIG. 8) that attaches to the frame attachment region 114

(e.g., using an adhesive bond or a mechanical gland/seal configuration). FIG. 7B and FIG. 8 illustrate attachment of the membrane attachment region 116 to the frame attachment region 114. The flexible membrane 104 can have a dome shape (e.g., an elongated dome shape) with the membrane attachment region 116 located at the base of the dome shaped flexible membrane 104 (e.g., around the perimeter of the base). When the base surface 112 is resting on a supporting structure, the dome-shaped flexible membrane 104 may protrude upwards from the device frame 102.

When the flexible membrane 104 and the device frame 102 are attached together, the device frame 102 and the flexible membrane 104 at least partially enclose a dome-shaped pressure chamber 108 between the device frame 102 and the flexible membrane 104. The dome-shaped pressure chamber 108 can be sealed at an interface between the device frame 102 and the flexible membrane 104. Depending on the implementation of the pressure-sensing device 100, additional seals and components (e.g., a pressure sensor 110 and/or circuit board) may define a portion of the pressure chamber 108. The interface between the flexible membrane 104 and the device frame 102 (e.g., between the membrane attachment region 116 and the frame attachment region 114) and the additional seals may form a substantially airtight seal for the pressure chamber 108. In some implementations, the pressure chamber 108 may be air-tight enough to withstand the pressure of a seated user for the duration of a workout (e.g., approximately 5 minutes or more) or multiple workout sessions.

The pressure-sensing device 100 may include a pressure sensor 110 that is at least partially included within the pressure chamber 108. In one example, with respect to FIG. 10, the pressure sensor 110 can be completely included within the pressure chamber 108. In another example, with respect to FIG. 6 and FIG. 8, the pressure sensor 110 can protrude into the pressure chamber 108 through an opening in the device frame 102. The pressure sensor 110 is configured to generate a pressure signal indicating the pressure in the pressure chamber 108. The pressure sensor 110 may transmit the pressure signal to the device electronics in either an analog or digital format. The pressure sensor 110 may detect the pressure as an analog value, and in the case of a digital output, the analog value may be converted to a digital representation and transmitted using a digital communication protocol, such as via an inter-integrated circuit (I2C) bus or serial peripheral interface (SPI) bus. In both cases, the pressure signal that is transmitted to the device electronics may indicate the pressure in the pressure chamber 108, with varying degrees of accuracy and amplification. With some digital pressure sensors, the output can be scaled to one of a variety of ranges in order to allow the same pressure sensor to be used in a variety of pressure range environments. This may allow for dynamically changing the sensitivity of the pressure-sensing device 100 without having to change the physical amplification circuitry.

The pressure-sensing device 100 may include additional electrical/electronic devices (e.g., in addition to the pressure sensor 110), which may be referred to herein as "device electronics." The device electronics can be connected to the device frame 102 and can be electrically coupled to the pressure sensor 110. The device electronics are configured to receive the pressure signal and determine the pressure in the pressure chamber 108 based on the pressure signal. The device electronics can include, but are not limited to, signal conditioning electronics (e.g., amplifiers and/or filters), power electronics (e.g., voltage regulators), communication electronics (e.g., WiFi, Bluetooth, and/or universal serial bus (USB)), and user interface electronics (e.g., buttons/switches, vibration devices, lighting devices). The device electronics may also include battery and power management electronics along with charging circuitry. Although the device electronics are illustrated herein as being connected to the device frame 102, the device electronics can be included in any location inside or outside of the pressure-sensing device 100 (e.g., inside or outside of the device frame 102 and/or flexible membrane 104). For example, some or all of the device electronics may be attached to a portion of the flexible membrane (e.g., a tab on the flexible membrane included inside the pressure-sensing device 100).

A user can interact with the pressure-sensing device 100 in a variety of different ways. For example, the user may interact with the pressure-sensing device 100 using manual user interface components (e.g., a user input button) and/or using a wired/wireless user computing device (e.g., a smartphone). In some implementations, the user can download and install an application that communicates with the pressure-sensing device 100. Such an application executed on a user computing device may interact with the pressure-sensing device 100, monitor a user's workout, and provide other functionality.

Figure 19A:
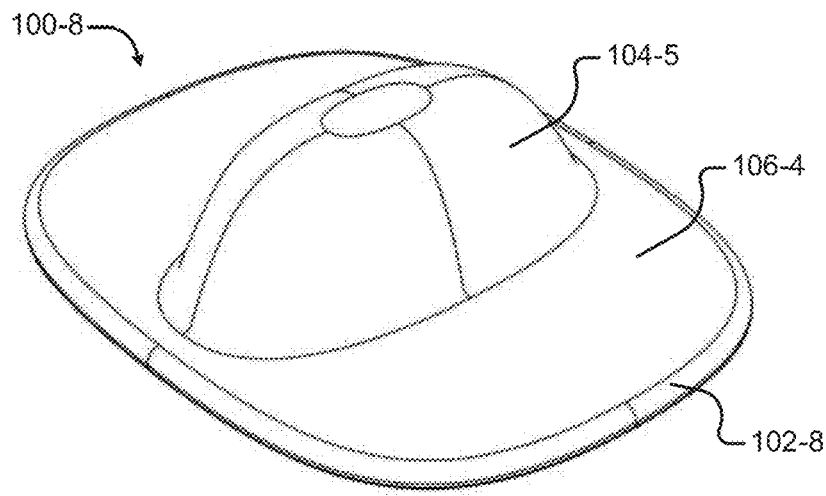
Figure 20:
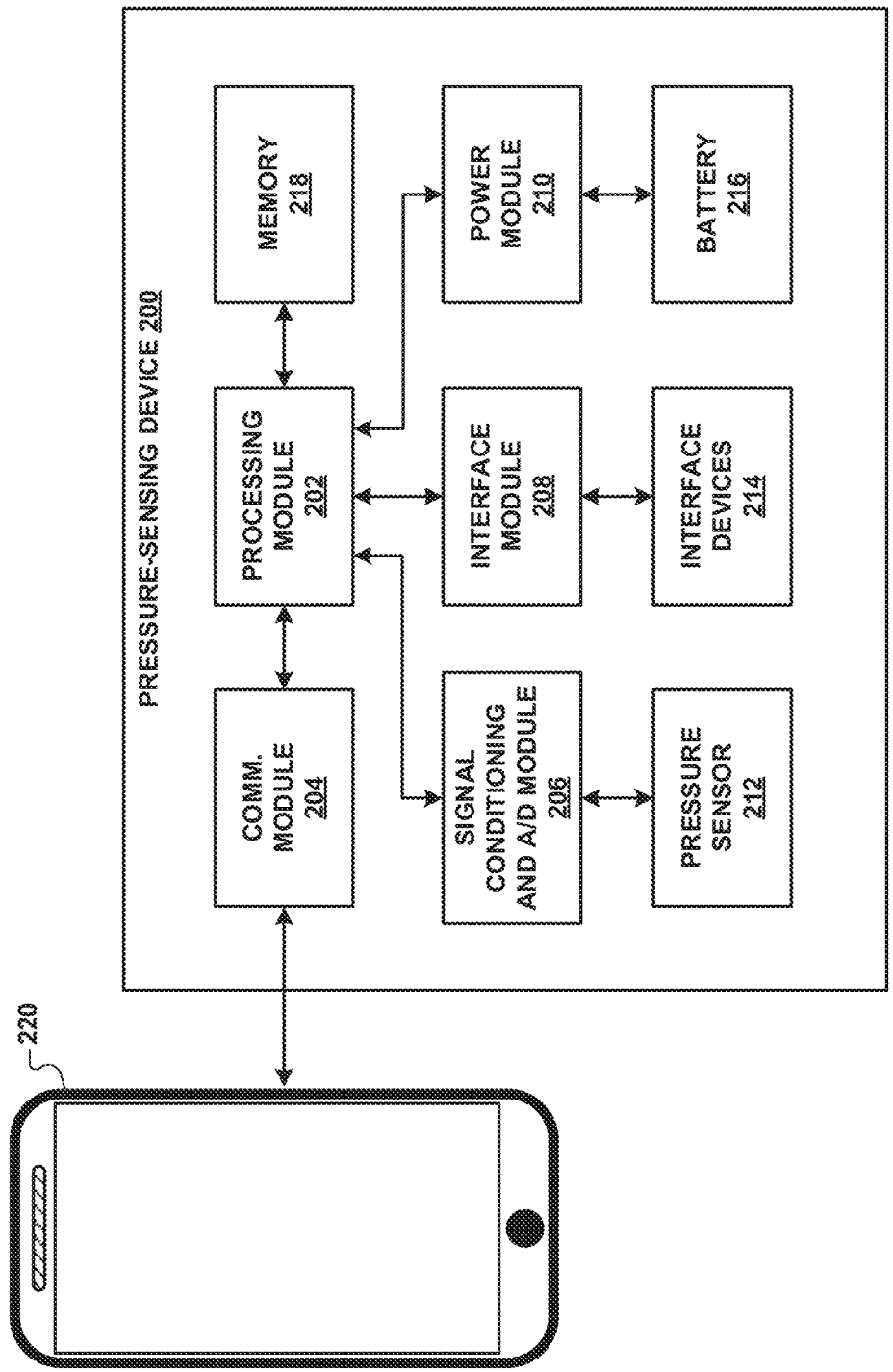
FIG. 20 is a functional block diagram of a pressure-sensing device in communication with a user computing device.
Figure 21:
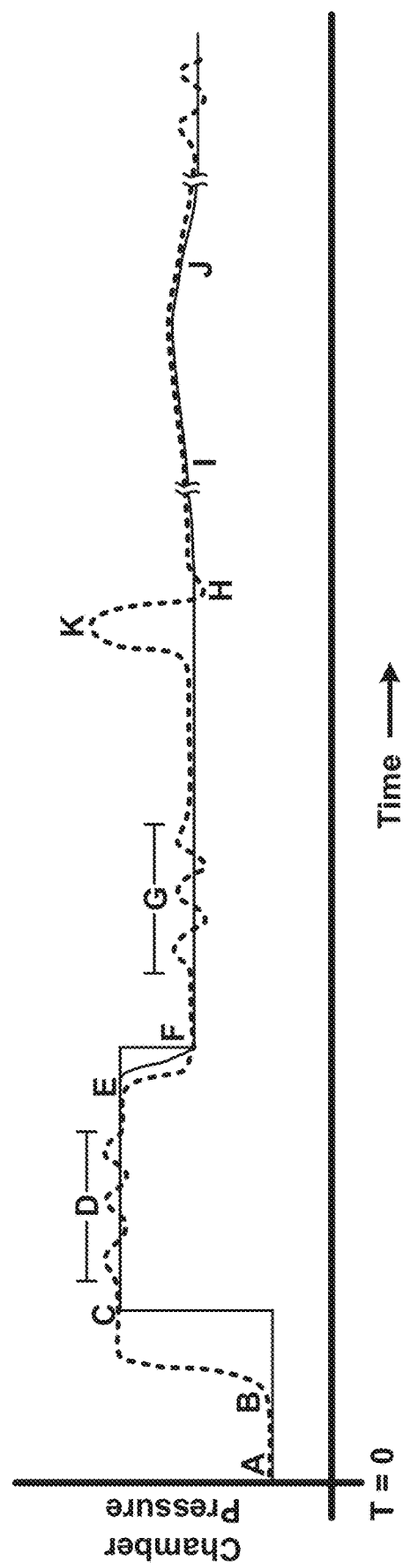
FIG. 21 is a graph that illustrates chamber pressure within a pressure-sensing device and a reference value generated by the pressure-sensing device over time while a user is using the pressure-sensing device.

FIGS. 1A-3B illustrate example external features of the pressure-sensing devices 100. FIGS. 4-15 illustrate example internal features of the pressure-sensing devices 100. FIGS. 16A and 16B illustrate a user holding the pressure-sensing devices 100 in their hand. FIGS. 17-19F illustrate additional form factors of the pressure-sensing devices 100. FIG. 20 is a functional block diagram of the pressure-sensing device 100. FIG. 21 illustrates an example pressure signal generated by the pressure sensor 110. FIGS. 22A-22D illustrate example graphical user interfaces generated on a user computing device that interacts with the pressure-sensing device 100. The pressure-sensing devices 100 illustrated and described with respect to the figures are example implementations of pressure-sensing devices. As such, the pressure-sensing devices 100 illustrated in the figures may be modified. For example, some features described herein can be added to, or removed from, the different pressure-sensing devices 100.

FIGS. 1A-2E illustrate external features of an example pressure-sensing device 100-1. The pressure-sensing device 100-1 includes a flexible membrane 104 (e.g., a dome-shaped flexible membrane). The flexible membrane 104 may be highly flexible, such that it may conform to the human body and flex in response to small displacements caused by muscle contractions. The flexible membrane 104 may be elastic, such that it can rebound to its original shape when unloaded. As part of the pressure chamber 108 (e.g., FIG. 4), the flexible membrane 104 may not allow air to freely flow through it, although minimal air diffusion through the flexible membrane 104 may occur over long periods of pressurization. It may be advantageous if the flexible membrane 104 can be easily cleaned. For example, the flexible membrane 104 may not readily absorb water, so that it can be wiped clean as needed. The flexible membrane 104 can also be formed from a material that is safe for body contact.

The flexible membrane 104 may be formed from materials, including, but not limited to, silicones, TPEs (thermoplastic elastomers), TPUs (thermoplastic urethanes), or other elastomeric materials. The flexible membrane 104 may be molded as a stand-alone component that is assembled into the final device, or it may be co-molded or over-molded onto one of the frame components of the device. For a silicone membrane, the manufacturing method may include either compression molding or Liquid Injection Molding (LIM) of a 2-part liquid silicone rubber (LSR) material, with the addition of pigment to control the membrane color, for example.

The flexibility and elasticity of the flexible membrane 104, an elastomeric material, may be represented by a durometer rating. By adjusting the geometry of the flexible membrane 104 (e.g., material thickness) together with the durometer, it may be possible to tune the way the flexible membrane 104 feels when it is deformed (e.g., how difficult it is to deform as well as how quickly it rebounds when the load is removed). A higher durometer (stiffer material) may be coupled with a thinner material to achieve a similar feel to a design with a lower durometer (softer material) and thicker material. In one example pressure-sensing device, a silicone flexible membrane with a durometer of 25 A-40 A (e.g., 35 A) and a thickness of 1 mm-2 mm (e.g., 1.5 mm) can be used.

The flexible membrane 104 can be formed to include a variety of features that provide for assembly to the device frame 102. For example, the flexible membrane 104 may include 1) indexing features that help align the flexible membrane 104 with the device frame components, 2) sealing/gland geometry to create or enhance the air-tight seal of the pressure chamber 108, and 3) adhesive promotion features to help reinforce a bond between the flexible membrane 104 and the device frame components. Combining these features into the flexible membrane 104 can reduce the number of components used in assembly.

The device frame 102 may be formed from a more rigid material than the flexible membrane 104. The device frame 102 may be configured to withstand the weight of a user sitting on the pressure-sensing device 100 (e.g., refrain from flexing). For example, the flexible membrane 104 may deform when a user sits on the pressure-sensing device 100, while the device frame 102 maintains the original unstressed shape. The device frame 102 may be formed from rigid materials, such as plastics and/or metals. In some implementations, the device frame 102 may be molded from an elastomeric material that is of higher durometer than the flexible membrane 104. This may allow for a quasi-flexible frame that could conform somewhat to the body, thereby making it more comfortable to use.

Figure 1B:
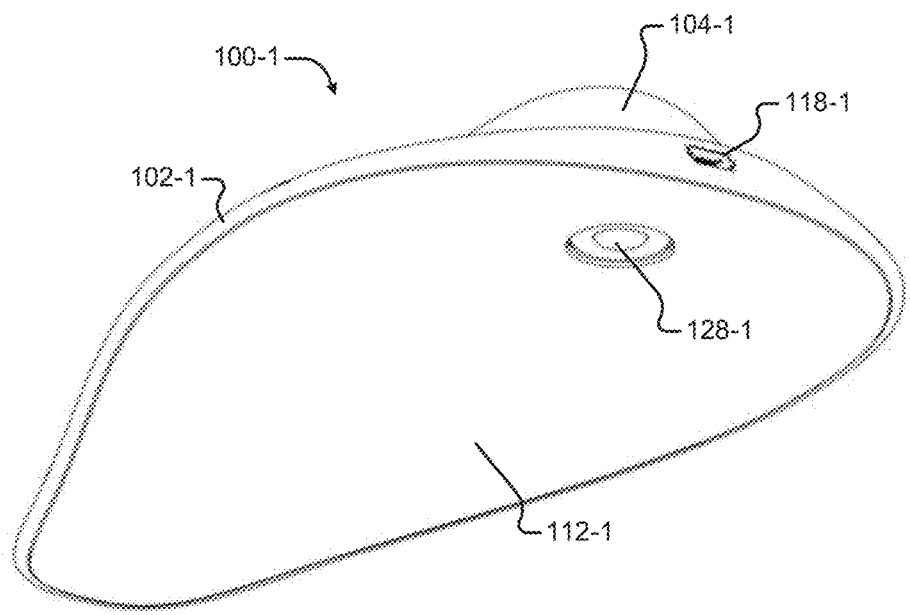
Figure 3A:
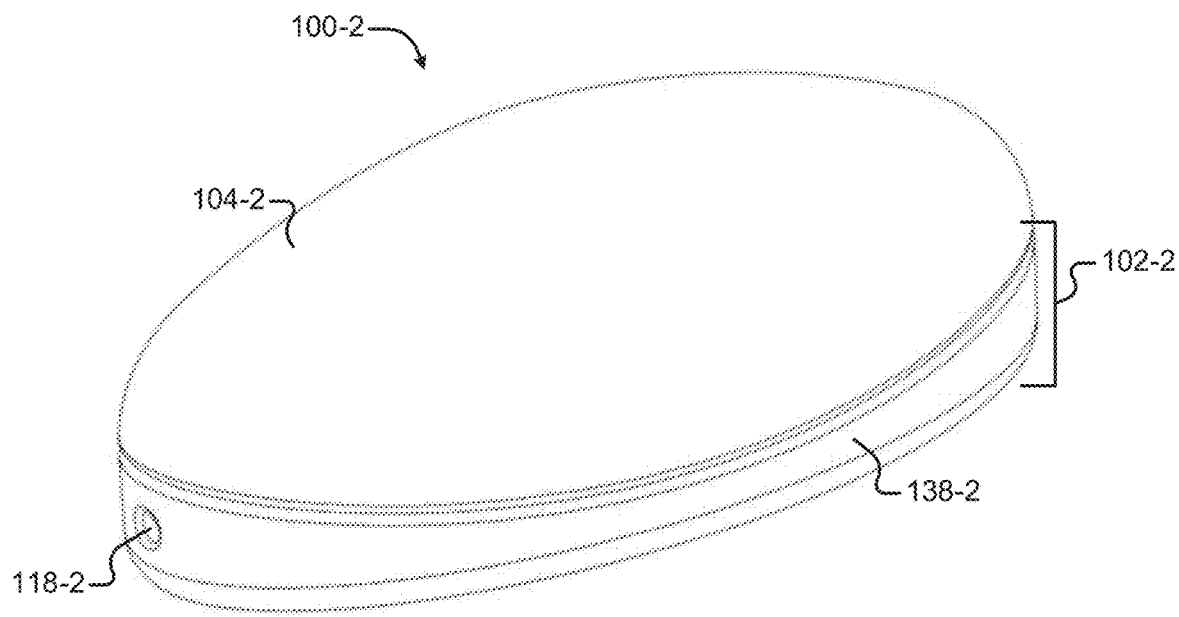
FIGS. 3A-3B illustrate a second example pressure-sensing device.

The pressure-sensing devices 100 may include a charging port 118 configured to receive a wired power plug (e.g., from a wall adapter). For example, the device frames 102-1, 102-2 of FIGS. 1B and 3A include charging ports 118-1, 118-2 through which a charging cable may be inserted. In the example of FIG. 1B, the illustrated charging port 118-1 is a USB port configured to receive a USB connector/cable for charging a battery 120 (see FIG. 5, FIG. 7D, and FIG. 8A) of the pressure-sensing device 100-1. In the example of FIG. 3A, the charging port 118-2 is configured to receive a barrel plug connector for charging a battery included in the pressure-sensing device 100-2.

In some implementations, the pressure-sensing device 100 can include a data transfer port, such as the USB port 118-1 illustrated in FIG. 1B. In these implementations, the pressure-sensing device 100 can include a single port (e.g., a USB port) that provides for both power and data transfer. In implementations where one or more ports (e.g., charging and/or data transfer ports) are included in the device frame 102, the ports may include port seals (not illustrated) that make the ports waterproof and/or airtight. For example, with respect to FIG. 15, the ports may include port seals that maintain an airtight seal for the pressure chamber 108. In implementations where a waterproof/airtight device frame is not required (e.g., FIG. 1B and FIG. 3A) because the pressure chamber 108 is separated from the ports 118, the port seals may be optional.

In some implementations, the device frame 102 may include wireless charging circuits and/or wireless data transfer circuits. Wireless charging circuits may include electronics inside the pressure-sensing device 100, such as an antenna and power management electronics to capture the electromagnetic energy reaching the pressure-sensing device 100, as well as an external charging base station to transmit power to the pressure-sensing device 100 as electromagnetic energy. A large flat base surface may be desirable for wireless charging in order to maximize the cross-sectional area of a receiving antenna as well as minimizing the distance between the emitter and receiver antennas.

The pressure-sensing device 100 may include any form of wireless communication technology. Example wireless communication technologies may include, but are not limited to, Bluetooth (e.g., Bluetooth 4.0) and WiFi (e.g., 2.4 and/or 5.0 GHz). Such wireless communication technologies may be common in smart phones, laptops, and other personal electronic devices.

Figure 3B:
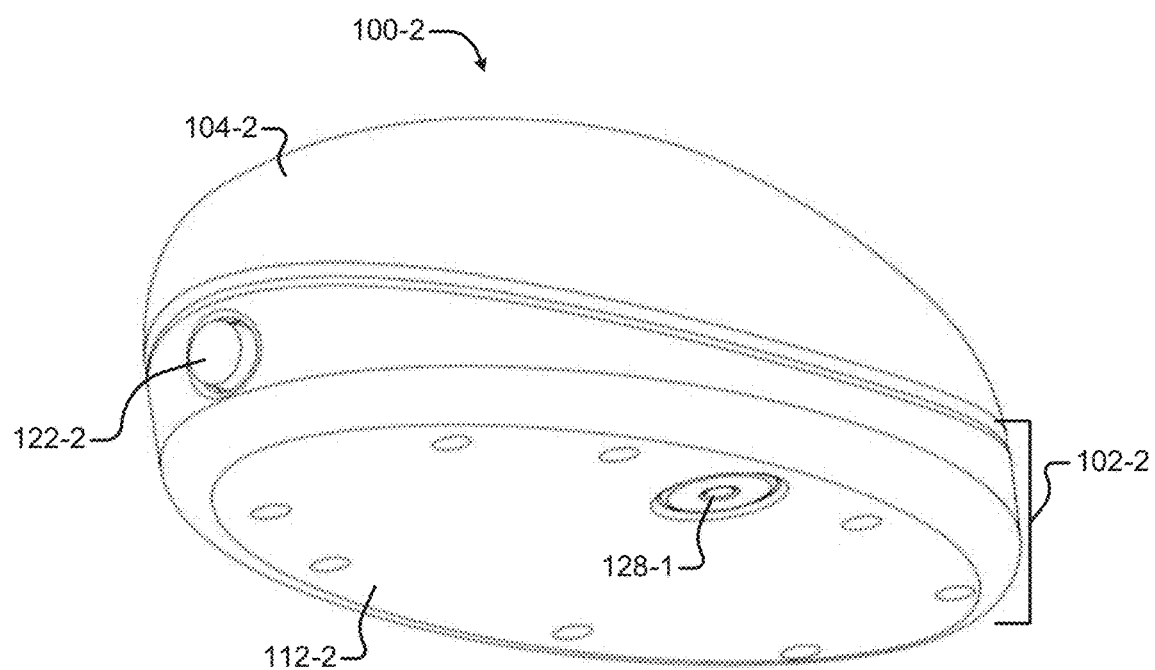

The pressure-sensing device 100 can include a variety of different user input components. For example, the pressure-sensing device 100 can include a user input button 122 (e.g., 122-1, 122-2 of FIG. 1A and FIG. 3B) that can be used for calibrating the pressure-sensing device 100 and/or turning the pressure-sensing device 100 on/off. Other user input options may include capacitive touch-sensors, inertial sensors (accelerometer, gyroscope, magnetometer), audio sensors (microphone), photo-sensors (light detection), hall effect or other magnetic sensors, as well as the pressure sensor 110 itself. User input may also be received by the pressure-sensing device 100 in the form of commands/instructions from another user device (e.g., 220 of FIG. 20) via wireless communication. The user input button 122 can be located on the device frame 102 such that a user can access the user input button 122 while the user is sitting on the pressure-sensing device 100 with the pressure-sensing device 100 placed in the perineum region of the user. For example, as illustrated in FIG. 1A, the user input button 122-1 can be located on the top of the device frame 102 (e.g., on the seating surface 106-1). As another example, as illustrated in FIG. 3B, if the pressure-sensing device 100-2 has an ellipse shape, the user input button 122-2 can be located at the edge of the device frame 102-2 intersected by the major axis of the ellipse. This edge of the device frame 102-2 may be positioned toward the front of the user during exercise and the user may access the user input button 122-2 by reaching between their legs during exercise.

The pressure-sensing device 100 can include a variety of different feedback components (e.g., a vibrating motor 124, lights 126, speaker) that indicate device events or a device status to the user. The feedback components may include one or more vibrating feedback components that indicate device events and/or a device status to the user by creating vibrations in the pressure-sensing device 100. An example vibration component may include a vibrating motor 124 (see FIG. 6) with an off-center mass. Other example vibration feedback components may include harmonic oscillators or pressure-wave generating elements.

The feedback components may also include one or more visual feedback components, such as a light emitting component 126 (e.g., a light emitting diode (LED)). For example, the device frame 102-1 of FIG. 1A includes a light emitting diode 126. The visual feedback components may indicate device events and/or a device status to the user by providing a visual cue (e.g., emitting a light). The visual feedback components may be included on the exterior of the device frame 102, integrated with the ports (e.g., charging/data ports), and/or included in the pressure chamber 108. In implementations where the visual feedback components are included in the pressure chamber 108, visual feedback may be provided through the flexible membrane 104. For example, a light emitting device (e.g., an LED) may illuminate the pressure chamber 108 and emit some light through the flexible membrane 104. In these examples, the flexible membrane 104 may appear illuminated.

The feedback components may also include one or more audible feedback components, such as a speaker. The speaker may indicate device events and/or a device status to the user via speech or other audible noises (e.g., beeps). In some implementations, a very low frequency audio signal may be used to provide feedback to the user. For example, because the pressure chamber 108 is in contact with the user's body, a very low frequency (e.g., sub-20 Hz) energy may be imparted into the pressure chamber 108 that may be felt by the user, but may be inaudible to the ear. Alternatively, an audible speaker could be used to provide information to the user. In one case, the speaker could be used to play music or speak to the user to provide encouragement during the workout in the case of using the pressure-sensing device 100 without a user device 220 (e.g., a smartphone). For example, the user may follow along with the suggested workout by listening to the instructions.

In some implementations, various interactions/games can be implemented using the feedback element. For example, a game including pattern memory and repetition may be implemented in which the pressure-sensing device 100 prompts the user to contract using a feedback element in various ways. In one example, the feedback element may request a pattern/strength of contraction by delivering feedback to the user via a signal (e.g., a vibration) having a specific pattern/strength. In response to the signal, the user may contract using a similar pattern/strength to that of the signal.

The feedback components described above may indicate a device status and/or a variety of different device events associated with the pressure-sensing device 100. A device status and/or device event indicated by the various feedback components may include, but are not limited to, a device charging event (e.g., the battery 120 is being charged), a communication event (e.g., the pressure-sensing device 100 is connected to a user device 220 via wired/wireless communication), a user contraction event (e.g., the pressure-sensing device 100 detects a pressure change consistent with exercising), a battery status, and other device events or device status. In some implementations, the feedback components can indicate a level of pressure change (e.g., a strength of contraction) associated with exercising. For example, the vibration device can vibrate according to the strength of user contraction detected (e.g., stronger vibrations for stronger contractions). As another example, a visual feedback component may adjust the amount of visual feedback according the strength of a user contraction (e.g., increase light intensity for stronger contractions). As an additional example, an audible feedback component can adjust the level of audible feedback according to the strength of contraction (e.g., increase volume for stronger contractions). Other interactions could include, but are not limited to: 1) indicating to the user that he/she has reached the end of a workout, 2) a low battery indication, 3) indicating to the user that he/she has achieved some pre-set goal or reached some milestone (personal best, number of contractions in the day, or another exercise metric/goal), 4) indicating events occurring on the user device 220, such as receipt of a text message, phone call, or email, and 5) changes in inertial properties of the pressure-sensing device 100 (e.g., moving a certain amount or remaining still for some period of time).

Although the pressure chamber 108 may be sealed with a substantially airtight seal, air may travel across the seal (e.g., through potential leaks) and/or through the flexible membrane 104. In addition, the pressure inside the pressure chamber 108 may change over time due to atmospheric pressure changes (e.g., at different altitudes and weather conditions). In some cases, the pressure chamber 108 may become overly inflated or overly deflated, depending on atmospheric pressure changes.

Figure 11:
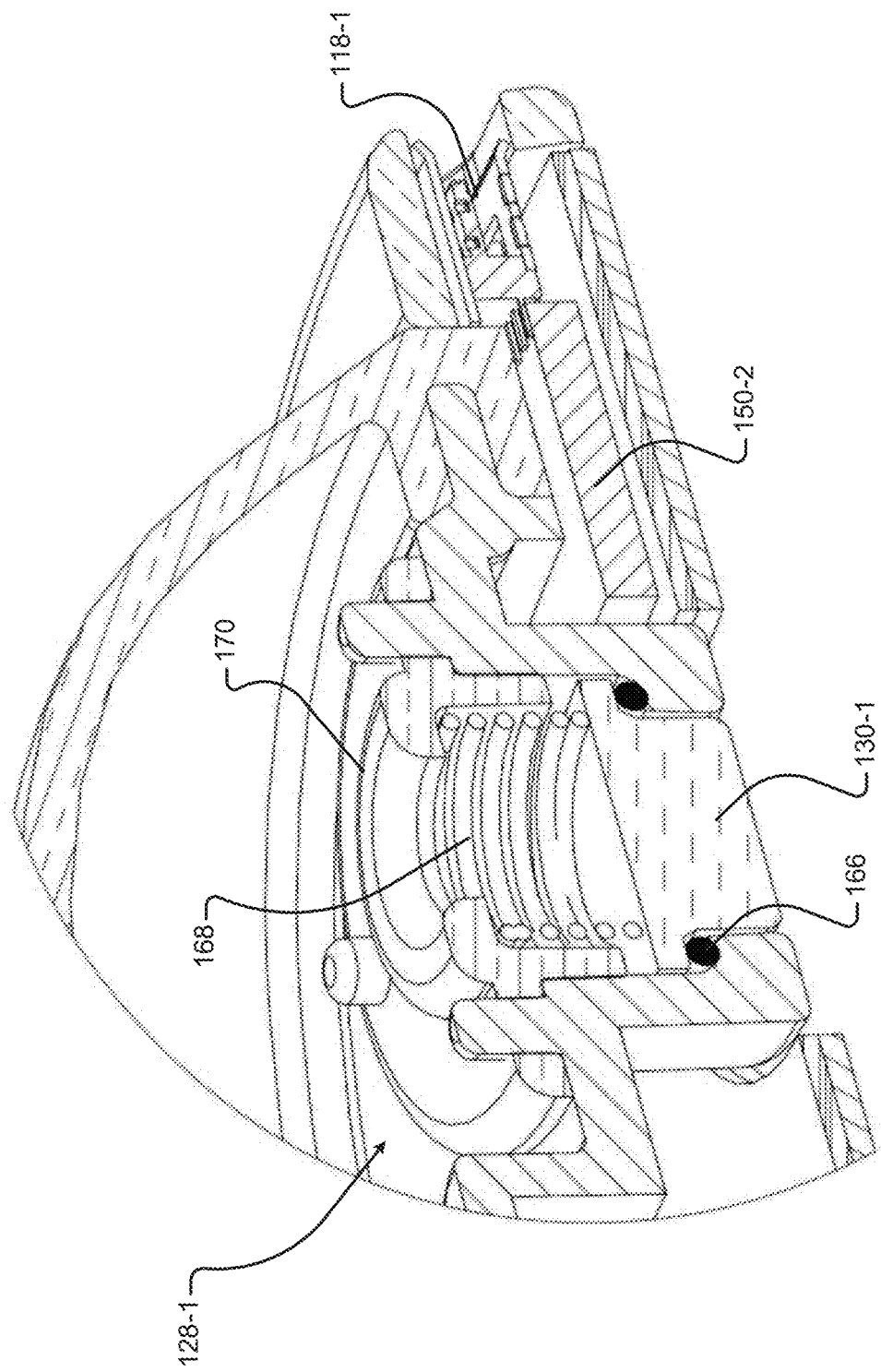
Figure 12:
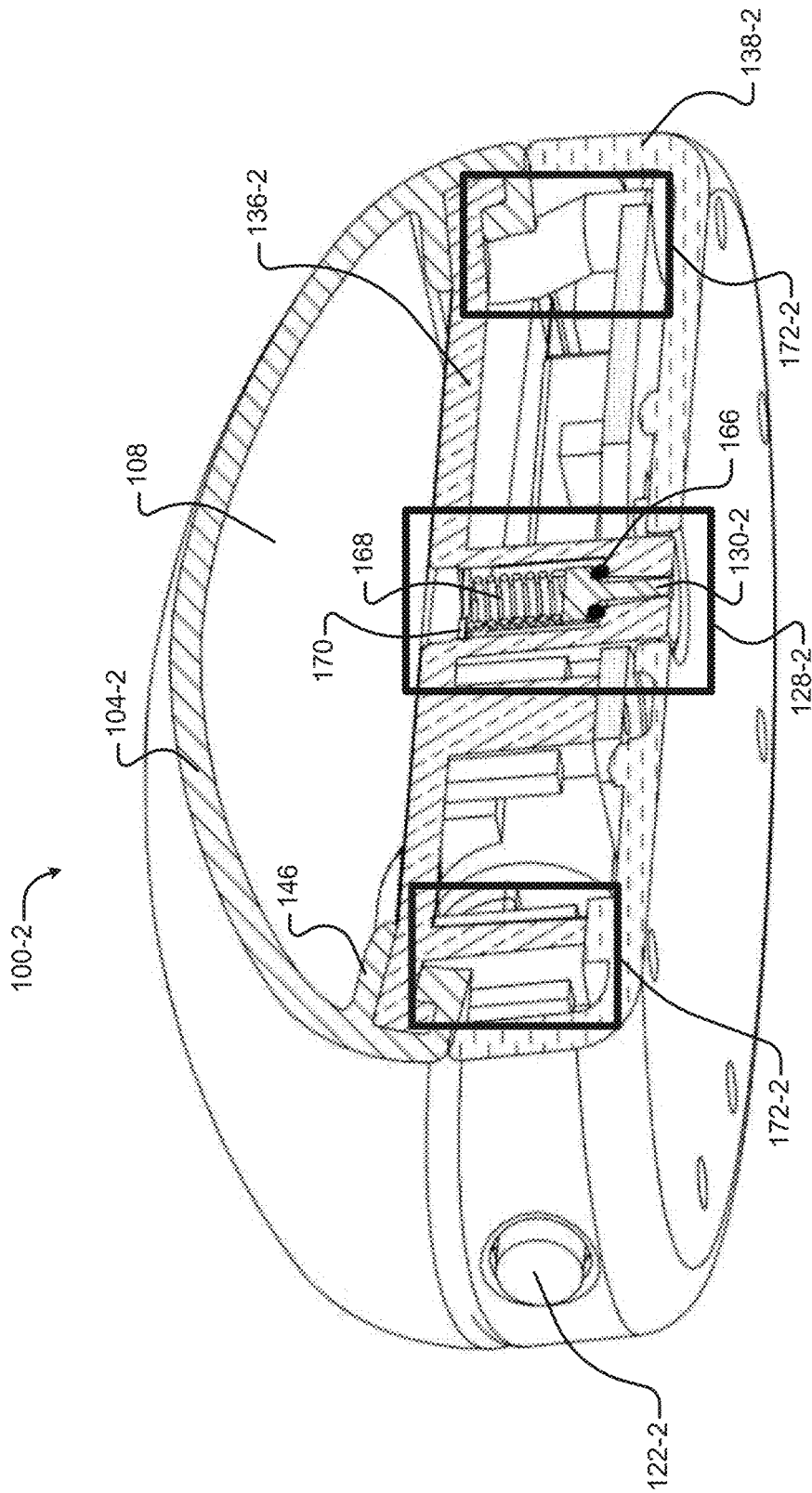
Figure 13:
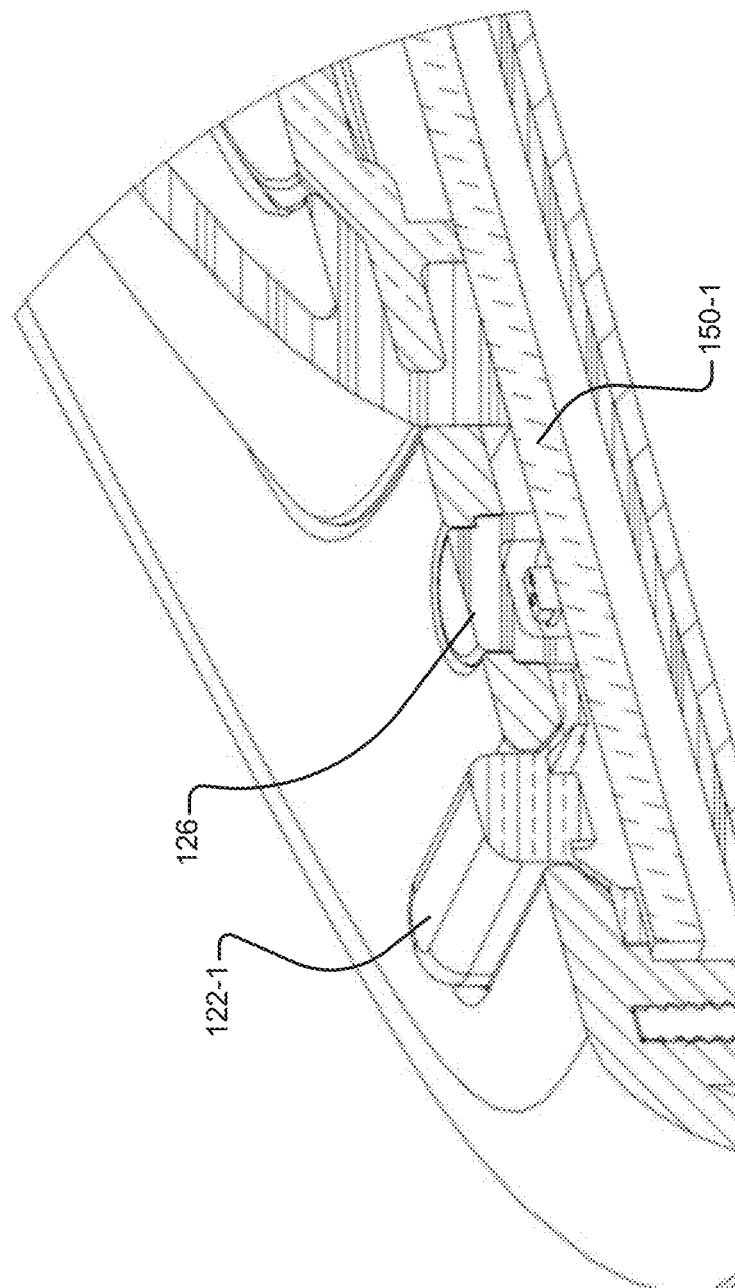

The pressure-sensing device 100 can include a vent assembly 128 (e.g., 128-1, 128-2 of FIGS. 11-12) that allows the user to equalize the pressure in the pressure chamber 108 with the pressure outside of the pressure-sensing device 100. In some implementations, the vent assembly 128 may extend from the pressure chamber 108 to the base surface 112. FIGS. 4-6 and FIG. 11 illustrate a first example vent assembly 128-1 in the pressure-sensing device 100-1. FIG. 12 illustrates a second example vent assembly 128-2 in the pressure-sensing device 100-2. The vent assemblies 128-1, 128-2 are now discussed in turn.

Figure 4:
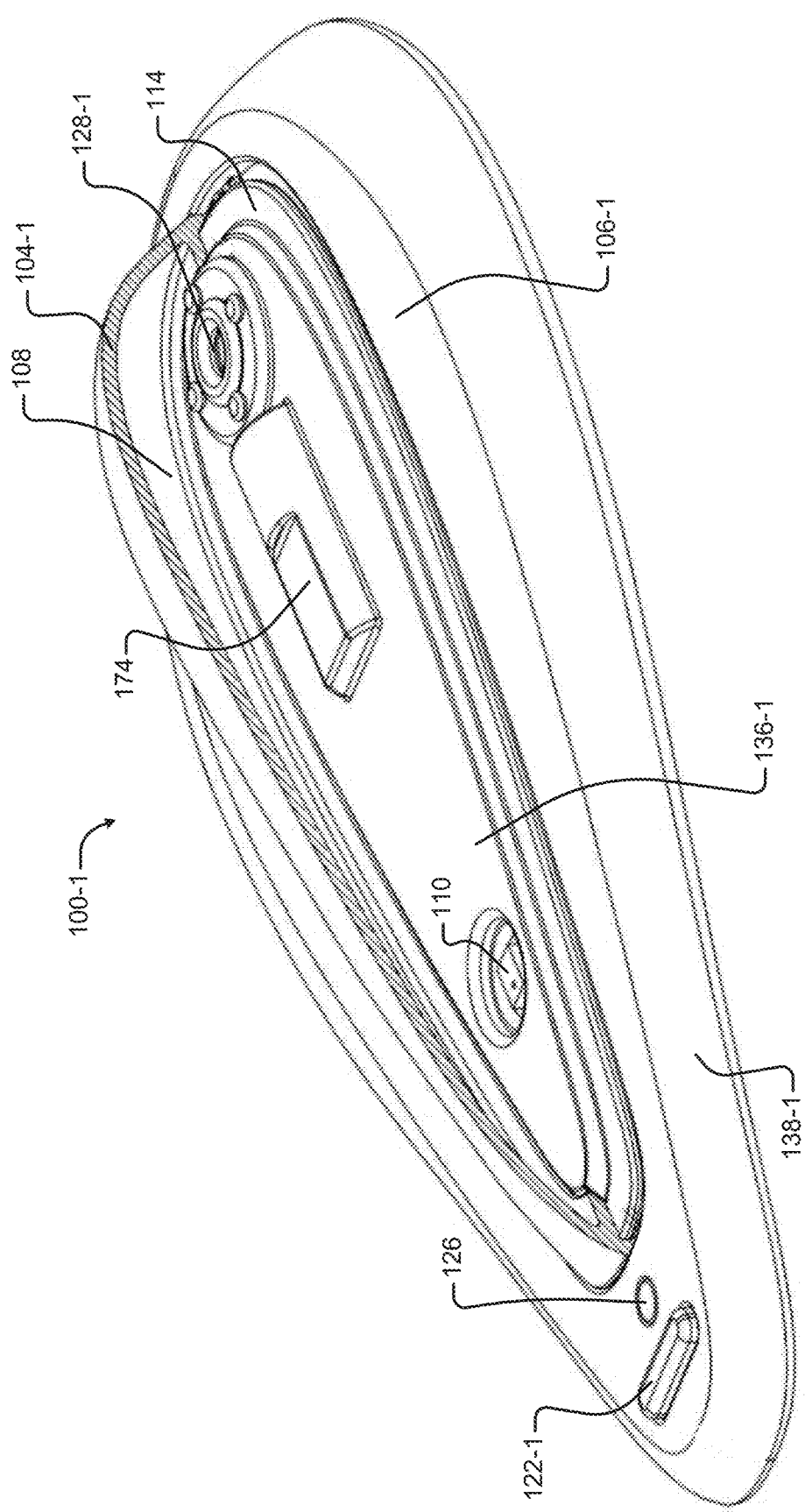
Figure 5:
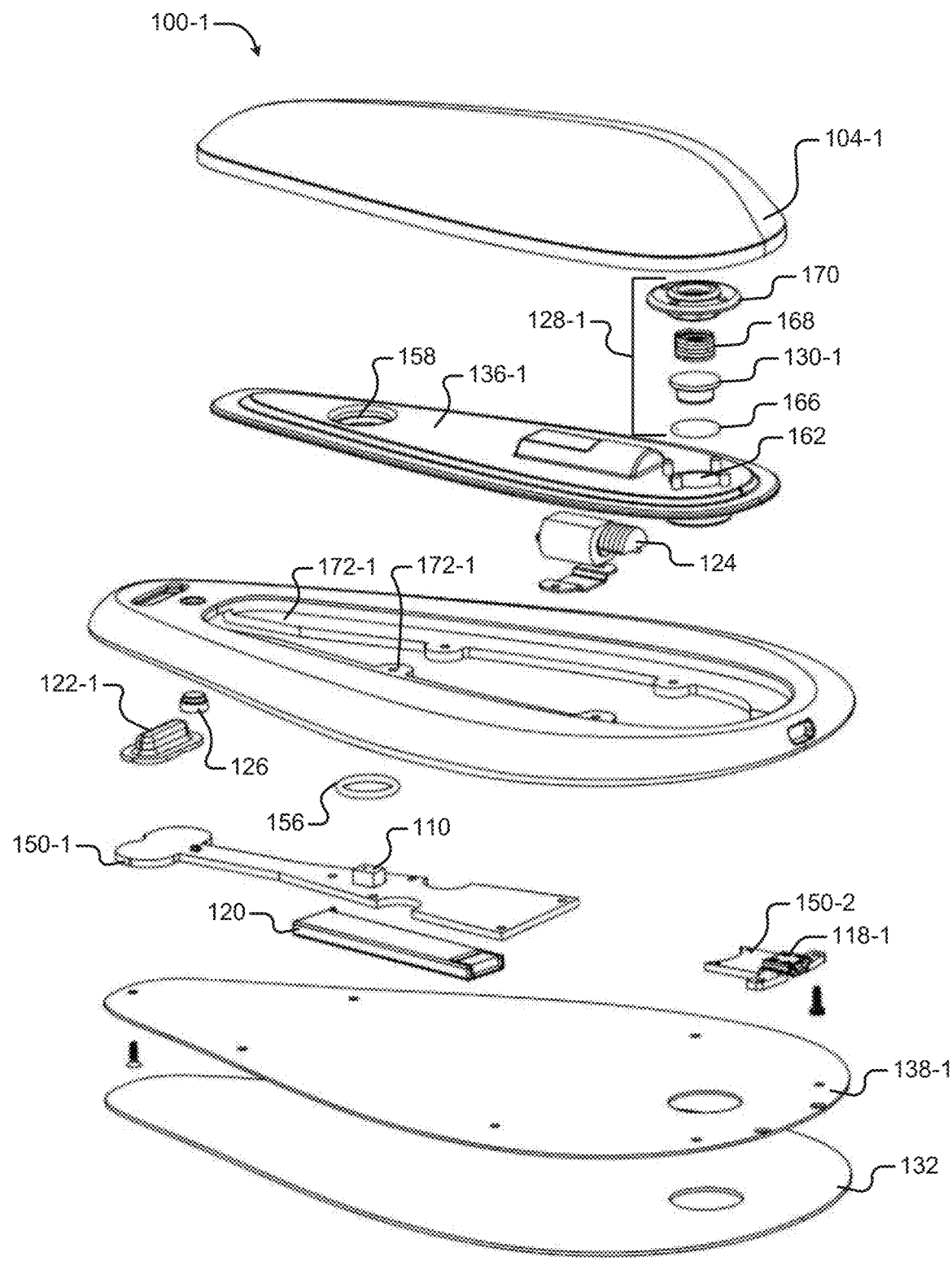

FIG. 1B illustrates a portion of the vent assembly 128-1 as viewed from the base surface 112-1 of the pressure-sensing device 100-1. FIG. 4 illustrates the portion of the vent assembly 128-1 included in the pressure chamber 108. FIG. 5 illustrates an exploded view of components included in the vent assembly 128-1. FIG. 11 illustrates a cross sectional view of the vent assembly 128-1 as assembled in the pressure-sensing device 100-1. FIG. 12 illustrates a cross sectional view of a vent assembly 128-2 having a different construction than FIG. 11. Referring to FIGS. 11-12, the vent assemblies 128-1, 128-2 may include vent shuttles 130-1, 130-2 that block airflow through the vent assemblies 128-1, 128-2 into the pressure chamber 108 when the vent shuttles 130-1, 130-2 are in a closed state. The vent shuttles 130-1, 130-2 may allow air transfer through the vent assemblies 128-1, 128-2 when the vent shuttles 130-1, 130-2 are in the open state. The user may manually depress the vent shuttles 130-1, 130-2 at the base surface 112 to open the vent shuttles 130-1, 130-2 and equalize the pressure in the pressure chamber 108 with the outside pressure. In some implementations, the pressure-sensing device 100 may include a fluid pump that can allow automatic or manual pressure changes of the pressure chamber 108, so that the pressure can be increased before, during, or after a workout in order to vary the shape or feel of the flexible membrane.

Although the vent assemblies 128-1, 128-2 are illustrated as included in the device frames 102-1, 102-2, in other implementations, a vent assembly may be integrated into the flexible membrane 104. A vent may be integrated into the flexible membrane in a variety of ways, including, but not limited to: 1) using a valve that is similar to a basketball needle valve (e.g., a long fluid pathway that can be opened by inserting the needle, and then which automatically closes when the needle is removed), 2) a duck-bill valve that can be molded directly into the flexible membrane material to reduce cost and complexity of assembly, and 3) a passive "valve" solution, such as a "Gore-tex" type membrane/barrier built into the pressure chamber to allow for very slow air flow in and out of the pressure chamber as natural pressure variations occur. This may allow for very slow equalization of pressure (such as resulting from weather changes), but may inhibit a rapid equalization.

Referring to FIGS. 1B and 3B, the device frame 102 includes a base surface 112 that may be configured to rest on an external supporting structure. Example external supporting structures may include a rigid (or semi-rigid) surface such as a mat or a magazine. The floor can also be used to provide an external resting surface. Soft surfaces, such as chairs and couches may also be used in some cases, but may benefit from the use of an additional support structure (such as a small pad/mat) in order to provide adequate support for the pressure-sensing device 100.

In some implementations, the base surface 112 can be formed from the same material as the rest of the device frame 102. In other implementations, the base surface 112 can be formed from a material that is different than the device frame 102. For example, the device frame 102 may include a base pad 132 (see FIG. 5 and FIG. 14) inserted into the underside of the device frame 102. The base pad 132 may form some (or all) of the base surface 112. In some implementations, the base pad 132 may be a single piece. In other implementations, multiple base pads (e.g., multiple feet) may be included on the base surface 112.

The base pad 132 may be made of metal (e.g., steel) or another material to add weight to the pressure-sensing device 100 in order to stabilize the pressure-sensing device 100 during use. The base pad 132 may also be made from a material that resists skidding of the pressure-sensing device 100 along the external supporting structure during use. For example, the base pad 132 may include a non-skid surface (e.g., rubber) that interfaces with the external supporting structure. The base pad 132 may also include a vibration dampening material (e.g., rubber) that dampens the transmission of vibrations through the external supporting structure. The base pad 132 may also include a cushioning layer. The non-skid layer, vibration dampening layer, and/or cushioning layer of the base pad may be included along with the weighting layer. For example, an adhesive backed rubber layer may be attached to the bottom of the device frame 102 and/or the weighting layer.

An external base pad/mat (e.g., 134 FIG. 19E) may be used when seated on a couch or seat cushion, such as in a car. The external base pad/mat may provide rigidity to support the pressure-sensing device 100 in response to muscle contractions. The external base pad/mat may be similar to a magazine in rigidity, or it may have varying rigidity in its 2 dimensions of surface, thereby allowing it to be preferentially rolled or folded when not in use (e.g., similar to a bamboo mat or sushi-rolling mat). The size of the external base pad/mat may vary. In one implementation, an example rectangular external base pad/mat may have dimensions of approximately 110 mm-150 mm per side.

In some implementations, the pressure-sensing device 100 may attach to the external base pad/mat. The attachment may be achieved through a connection, such as velcro or a mechanical latch/locking system. Additionally, or alternatively, the pressure-sensing device 100 may be fit into a corresponding pocket in the external base pad/mat, thereby preventing the pressure-sensing device 100 from sliding on the surface of the external base pad/mat. Additionally, or alternatively, magnets may be used (e.g., embedded in the pressure-sensing device 100 and/or the external base pad/mat) to index the pressure-sensing device 100 on the external base pad/mat and hold it in position, possibly with the help of a non-stick surface material to prevent lateral slip.

Figure 8A:
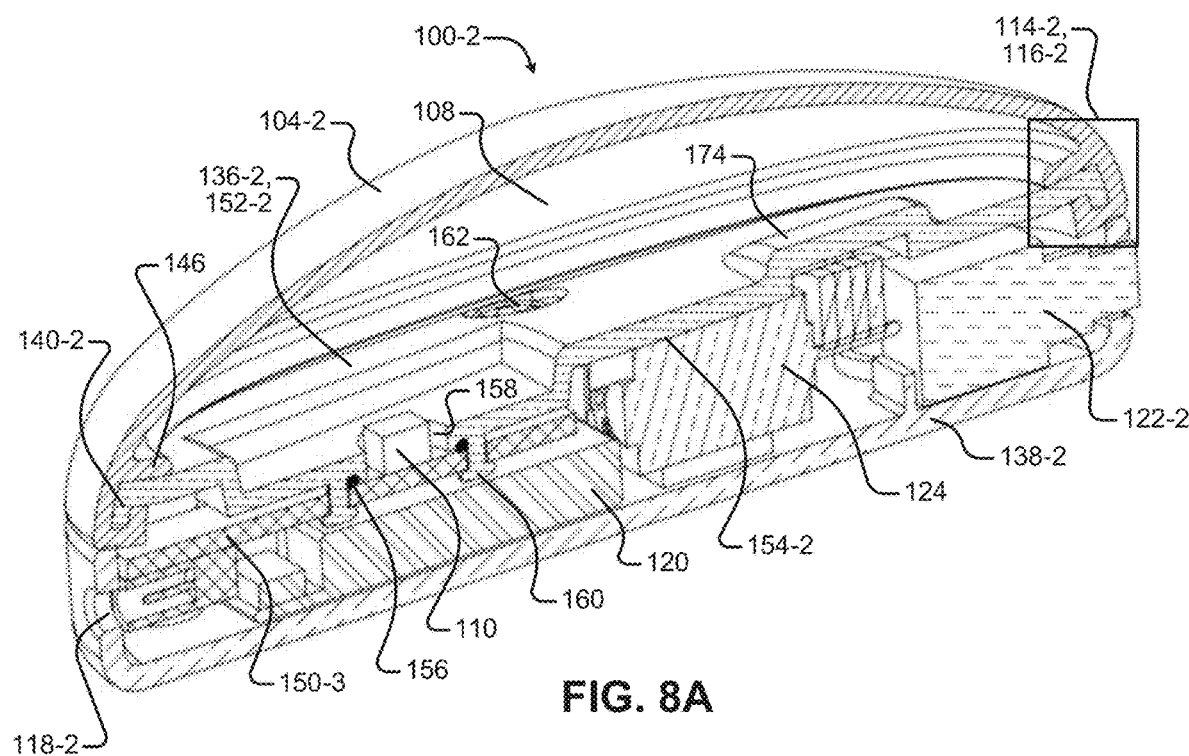
Figure 8B:
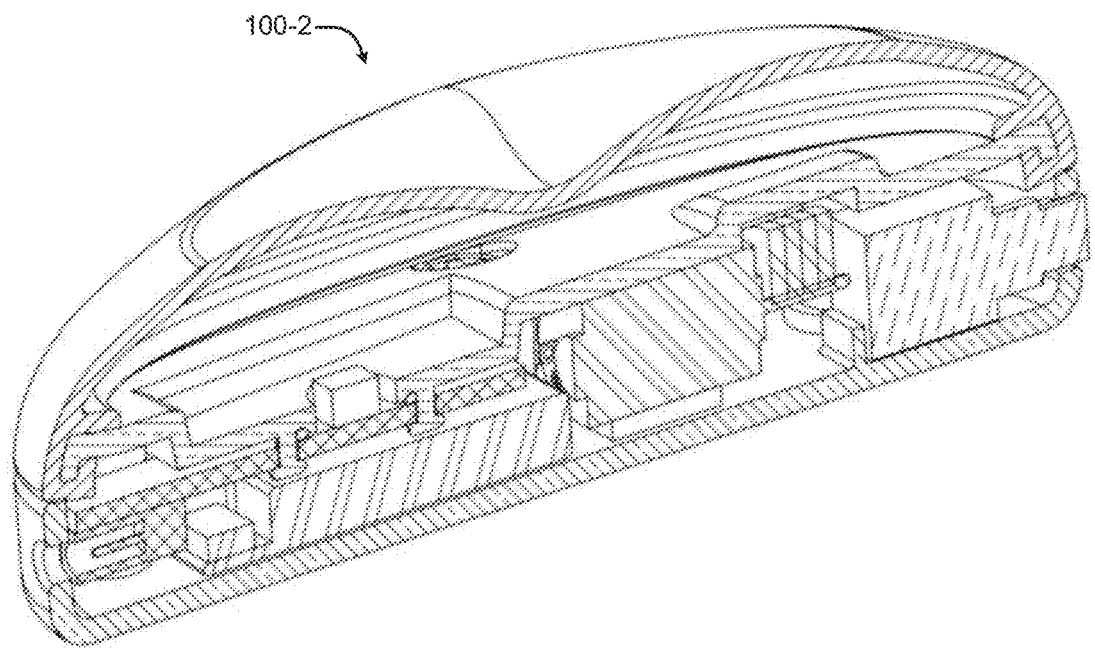

The device frames 102 illustrated herein include a membrane frame 136 (e.g., 136-1, 136-2 of FIG. 5 and FIG. 8A) and a base portion 138 (e.g., 138-1, 138-2 of FIG. 5 and FIG. 8A). In some implementations (e.g., 138-2 of FIG. 8A), the base portion 138 may be formed from a single rigid component. In other implementations (e.g., 138-1 of FIGS. 1A-2E), the base portion 138 may include more than two separate rigid frame components (e.g., as illustrated in FIG. 5). In some implementations of the pressure-sensing devices 100, the flexible membrane 104 attaches to the membrane 100, which in turn attaches to the base portion 138 (e.g., using frame fasteners such as screws). In other implementations (e.g., pressure-sensing device 100-5), the device frame 102 may be formed from a single frame component. Specifically, the device frame 102-5 may be formed from a single component that acts as a membrane frame 136-5 and base portion 138-4 that houses the device electronics within the pressure chamber 108.

Attachment of the flexible membrane 104 to the device frame 102 is described with respect to the pressure-sensing devices 100-1, 100-2 of FIG. 1A and FIG. 3A. Techniques for attaching the flexible membrane 104 to the device frame 102 (e.g., the membrane frame 136-1, 136-2) may be applicable to any of the pressure-sensing devices illustrated herein.

Although the flexible membrane 104 and membrane frame 136 are illustrated and described as being formed as separate components and then fit together, in some implementations, the flexible membrane and device frame may be formed in a different manner. For example, some soft plastics may be roto-molded or blow-molded to become a flexible membrane that is attached to the membrane frame. Although the flexible membrane 104 may be attached to the membrane frame 138 using an adhesive, in some implementations adhesives may not be used to connect the flexible membrane 104 to the membrane frame 136. Non-adhesive connection of the flexible membrane 104 and the membrane frame 136 may provide some benefits, including a simpler assembly and ease of disassembly/reuse of components if needed. An example non-adhesive connection may include a compressive face seal around the perimeter. In some non-adhesive connections, the sealing geometry may be molded into the flexible membrane 104.

The flexible membrane 104 and the membrane frame 136 are attached to each other. The flexible membrane 104 includes a membrane attachment region 116 (e.g., 116-1, 116-2 of FIG. 7A and FIG. 8A) that is formed to attach to a frame attachment region 114 of the membrane frame 136. The membrane attachment region 116 can be located at the base of the dome shaped region of the flexible membrane 104. For example, the membrane attachment region 116 can be located around the perimeter of flexible membrane 104.

When the flexible membrane 104 and the membrane frame 136 are attached to one another, the dome-shaped flexible membrane 104 may arch above the membrane frame 136 to form the pressure chamber 108 (e.g., a dome-shaped pressure chamber) between the flexible membrane 104 and the membrane frame 136. For example, the pressure chamber 108 may be defined by the arching interior surface of the flexible membrane 104 and a relatively flat, or slightly curved, membrane frame 136.

The perimeter of the membrane frame 136 (e.g., the frame attachment region 114) can have a flange 140 (e.g., 140-1, 140-2 of FIG. 7A and FIG. 8A) around which the membrane attachment region 116 may be fitted. The flange 140 may be formed around the entire circumference of the membrane frame 136. In some implementations, as illustrated in FIG. 8A, the frame attachment region 114 of the membrane frame 136 can have a flange 140 that points downward toward the base surface 112 of the device frame. In these implementations, the membrane attachment region 116 may wrap around the flange 140. For example, if the flange 140 points downward, the membrane attachment region 116 may wrap around the flange 140 and up under the downward protruding portion of the flange 140.

In some implementations (e.g., FIG. 14), the flange 140 may extend outward from the membrane frame 136 and then extend downward toward the base surface 112. In these implementations, the flange 140 may define a channel region 142 that extends around the membrane frame 136, the channel region 142 defined by the downward protruding flange 140 and the sidewall 144 of the device frame 102.

As described above, the membrane attachment region 116 can have a geometry that conforms to the membrane frame 136 (e.g., the frame attachment region 114). For example, the membrane attachment region 116 of the flexible membrane 104 may have an internal surface (e.g., continuous with the surface that defines the pressure region) that conforms to the surface of the membrane frame 136. For example, the internal surface of the flexible membrane may conform the flange 140 of the membrane frame 136.

In some implementations, the flexible membrane 104 may include a rib 146 (referred to herein as a "membrane rib 146") in the membrane attachment region 116. The membrane rib 146 extends into the inner portion of the dome-shaped flexible membrane 104. When the flexible membrane 104 is attached to the membrane frame 136, the membrane rib 146 is included in the pressure chamber 108 above the frame attachment region 114 of the membrane frame 136. The membrane rib 146 makes contact with the frame attachment region 114 and may be adhered to the membrane frame 136 at the frame attachment region 114. The membrane rib 146 may extend around the entire perimeter of the base of the flexible membrane 104 and may contact the frame attachment region 114 around the entire perimeter of the flexible membrane 104.

The flexible membrane rib 146 extends from within the pressure chamber 108 across the frame attachment region 114 towards the flange 140 of the membrane frame 136. The flexible membrane 104 then wraps around the flange 140. In implementations where the flange 140 forms a channel around the sidewall 144 of the membrane frame 136, the flexible membrane 104 may wrap around the flange 140 and up under the channel 142. The portion of the flexible membrane 104 that wraps under the flange 140 may be referred to as an "indexing lip." The indexing lip may be useful during assembly to ensure that the flexible membrane 104 is positioned correctly with respect to the membrane frame 136. Also, by wrapping around the membrane frame 136, the indexing lip may help prevent unwanted peeling of the edge of the flexible membrane 104 during use. As described above, the base of the flexible membrane 104 can contact the frame attachment region 114 around the perimeter of the membrane frame 136. Accordingly, the membrane rib 146 and the portion of the flexible membrane 104 that wraps around and conforms to the flange 140 may do so around the entire perimeter of the membrane frame 136, thereby forming an air-tight seal at the interface between the flexible membrane 104 and the membrane frame 136.

Prior to attachment of the flexible membrane 104 to the membrane frame 136, the membrane rib 146 and the portion of the flexible membrane 104 that conforms to the flange 140 may form a membrane channel 148 that is configured to be placed over the flange 140. The membrane rib 146 may provide a variety of benefits. For example, the membrane rib 146 may form a large adhesive surface area. Additionally, the membrane rib 146 may be configured such that pressure applied to the flexible membrane 104 may press the rib 146 against the membrane frame 136 rather than cause the membrane rib 146 to peel up from the membrane frame 136. In a sense, the membrane rib 146 may be self-energizing in that pressure generated in the pressure chamber 108 may cause the rib to be forced down onto the membrane frame 136. The increased adhesive area and the self-energizing nature of the membrane rib 146 may help maintain the airtight nature of the seal at the interface between the flexible membrane 104 and the membrane frame 136. The membrane rib 146 may also help to promote shear stress between the flexible membrane 104 and the membrane frame 136 (in the case of an adhesive seal) as opposed to tensile/peel stresses.

The flexible membrane 104 and membrane frame 136 can be adhered to one another at the interface between the flexible membrane 104 and the membrane frame 136. Adhesion between the flexible membrane 104 and the membrane frame 136 may be carried out in the following manner (in the case of a silicone flexible membrane and a plastic membrane frame):

1) Clean all relevant surfaces with a mild solvent such as isopropyl alcohol to remove any oils or other foreign materials and allow to dry.
2) Apply a very light coat of silicone adhesive primer to the membrane frame 136 in the area that will contact the adhesive. This may increase the surface energy of the plastic and increases the strength of the resulting bond with the silicone adhesive. Allow to fully dry (e.g., approximately 30 minutes).
3) Apply a silicone adhesive to the membrane frame 136 and/or flexible membrane 104 in the desired area (e.g., around the perimeter of the flexible membrane 104, between the membrane rib 146 and the indexing lip).
4) Fit the flexible membrane 104 over the membrane frame 136 such that the positioning matches the desired final positioning of the two components.
5) Place the assembly in a fixture that may be a negative form of the desired membrane/frame assembly. This may help to constrain the perimeter of the assembly to the correct geometry.
6) Allow the adhesive to cure (e.g., approximately 12 hours).

In some implementations, the membrane frame 136 may sandwich a portion of the flexible membrane 104 to create an airtight seal. The press fit seal may be in addition to the adhesive in some implementations. In other implementations, the press fit seal may be used as an alternative to the adhesive seal. Although a press fit seal is not illustrated in the figures, in alternative implementations of the pressure-sensing device 100, the flexible membrane 104 can be compressed between two other components (e.g., components included in the device frame 102, such as the membrane frame 136 and another component). The compressive force may create a face seal around the perimeter of the flexible membrane 104, thereby trapping the air inside the pressure chamber 108. Alternatively, there may be geometric features on the flexible membrane 104 that reinforces the seal when it is pressurized (e.g., similar to the membrane rib 146, but with more active features built in). These types of seals may be used with or without adhesive. Although the flexible membrane 104 is illustrated as wrapping around the membrane frame (e.g., at the frame attachment region), in some implementations, the flexible membrane may contact the frame attachment region on a single side (e.g., only a single side). In these implementations, the flexible membrane may be compressed against the membrane frame and/or adhered to the membrane frame to form a seal.

With reference to FIGS. 1A-2E, the device frame 102-1 (e.g., the base portion 138-1) includes a seating surface 106-1. The device frame 102-1 of FIGS. 1A-2E that includes a seating surface 106-1 may have a flattened-out geometry (e.g., a low profile shape) relative to the device frame 102-2 of FIGS. 3A-3B. Referring to FIG. 1A, the flexible membrane 104-1 protrudes above the seating surface 106-1. The seating surface 106-1 may extend outward around the base of the flexible membrane 104-1 and may provide a flattened surface for stabilizing the pressure-sensing device 100-1 during use. While using the pressure-sensing device 100-1, the flexible membrane 104-1 may be positioned in the user's perineum region while the seating surface 106-1 contacts the user in the perineum region, at the perimeter of the perineum region, and/or outside of the perineum region. While sitting on the pressure-sensing device 100-1, the user applies a downward force (e.g., toward the base surface 112-1) on the external support to prevent the pressure-sensing device 100-1 from moving during use.

The device frame 102 can have different shapes of seating surfaces 106. With respect to FIG. 1A, the device frame 102-1 forms a teardrop shape (e.g., similar to a bicycle seat). The flexible membrane 104-1 protrudes along the long axis of the teardrop shape to form an elongated pressure chamber 108 that may be placed in the user's perineum region during exercise. FIG. 19A illustrates an example pressure-sensing device 100-8 having a similar structure to the pressure-sensing device 100-1 of FIG. 1A, except that the pressure-sensing device 100-8 has a rectangular device frame 102-8. In general, the flexible membrane 104 protrudes from the device frame 102 in the center of the device frame 102 to form a centrally located protruding pressure chamber 108. Although the flexible membrane 104 is generally centrally located on the device frame 102 in the figures, in other implementations, the flexible membrane 104 may be off-centered with respect to the seating surface of the device frame (e.g., positioned forward or rearward on the rectangle/teardrop).

Although some of the seating surfaces 106 are illustrated as being composed of the same continuous pieces of material as the rest of the device frames 102, in some implementations, the seating surfaces 106 may include a material that is different than the rest of the device frame 102. For example, the seating surface may include a material that covers and/or cushions the seating surface, such as a portion of the flexible membrane (e.g., FIG. 18A) or other material. Although a flattened seating surface is illustrated, in some implementations, the seating surface may include contours that conform to a user's body.

Figure 6:
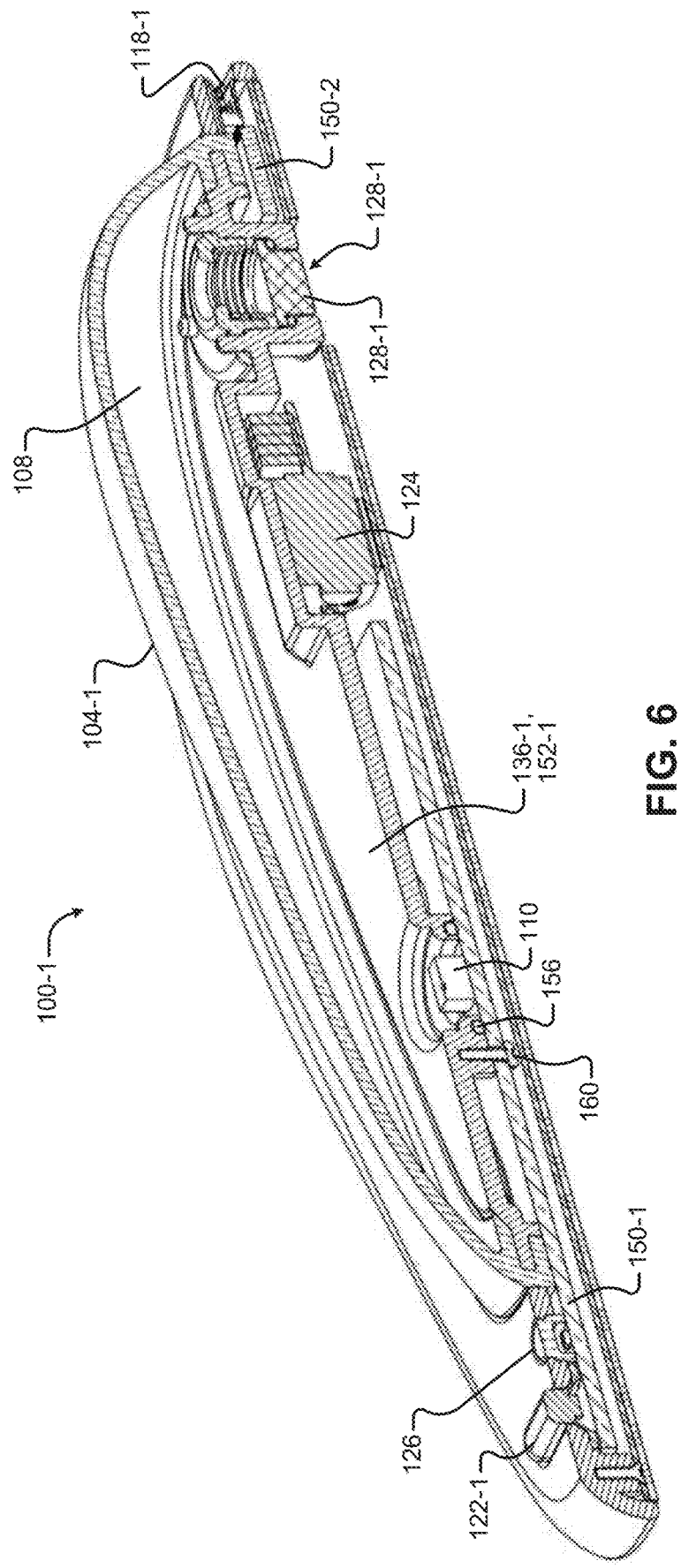
Figure 10:
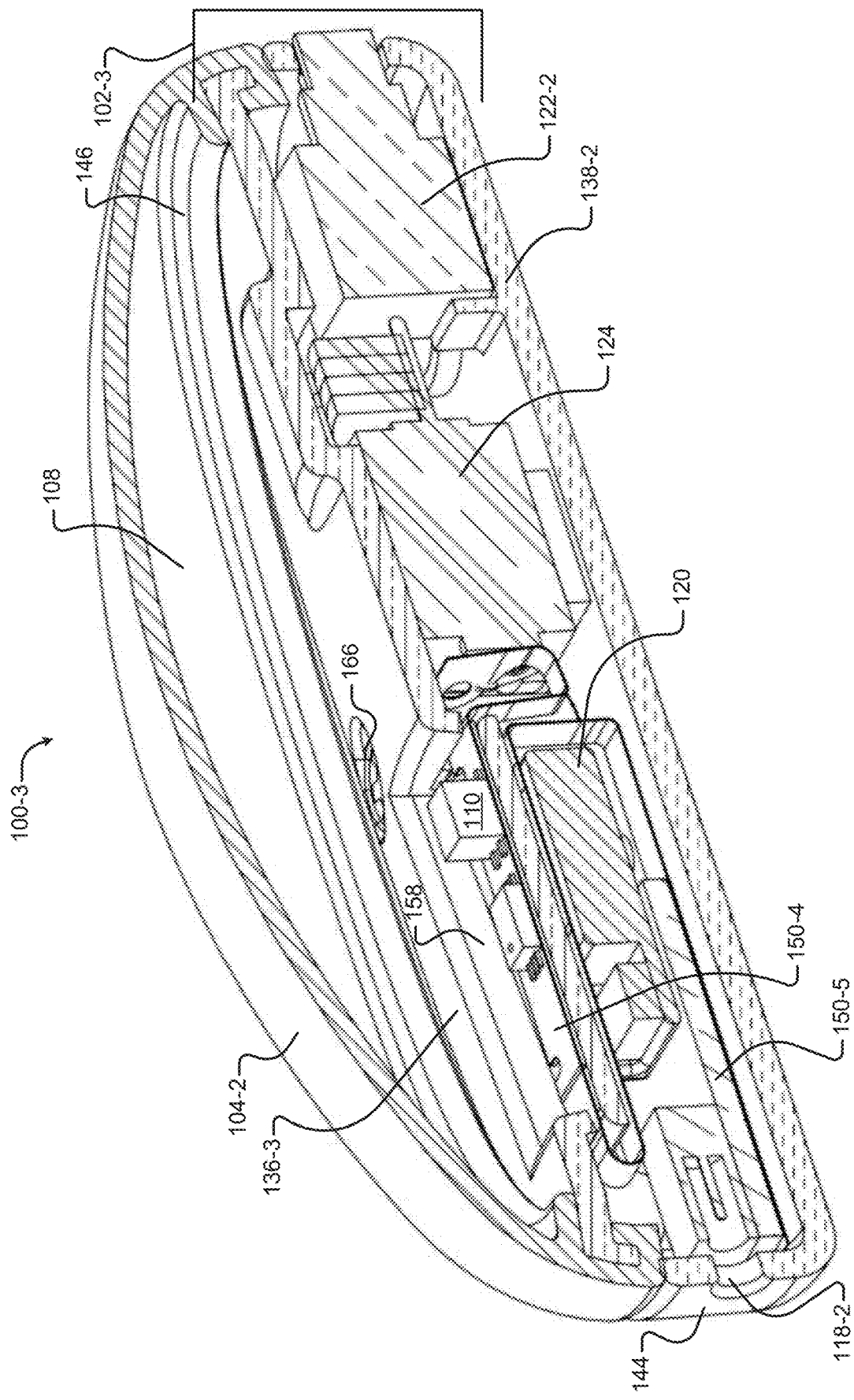

The membrane frame 136 and the base portion 138 define a chamber (referred to herein as the "electronics chamber") when the membrane frame 136 and the base portion 138 are fastened to one another. The electronics chamber may include the device electronics. Some of the device electronics can be directly attached to the device frame 102 (e.g., the membrane frame 136 and/or the base portion 138). Some of the device electronics can be included on one or more printed circuit boards (PCBs) 150 that are attached to the device frame 102. In FIGS. 5-6, and FIG. 10, the device electronics are included on two separate PCBs. In FIG. 8A, the device frame 102 only houses a single PCB.

The membrane frame 136 attaches to the base portion 138 and the flexible membrane 104. One surface of the membrane frame 136 may define a portion of the pressure chamber 108. The surface of the membrane frame 136 that defines a portion of the pressure chamber 108 may be referred to herein as the top surface 152 of the membrane frame 136 (e.g., 152-1, 152-2 of FIG. 7C and FIG. 8A). The surface of the membrane frame 136 that is opposite to the top surface 152 may define a portion of the electronics chamber. The surface of the membrane frame 136 that defines a portion of the electronics chamber may be referred to herein as the bottom surface 154 (e.g., 154-1, 154-2 of FIG. 7C and FIG. 8A) of the membrane frame 136.

In some implementations (e.g., pressure-sensing devices 100-1, 100-2), the electronics chamber may not be airtight, which may allow the pressure in the electronics chamber to fluctuate with the external pressure. In these implementations, the pressure chamber 108 and the electronics chamber may be sealed off from one another. For example, the pressure-sensing device 100 may include a frame seal 156 (see FIG. 9) that seals off the pressure chamber 108 from the electronics chamber. In other implementations (e.g., pressure-sensing device 100-5 of FIG. 15), the device electronics may be included in the sealed pressure chamber 108.

The membrane frame 138 defines a frame opening 158 (e.g., FIG. 5, FIG. 8A, and FIG. 10). The frame opening 158 can have a variety of different geometries, depending on the implementation of the pressure-sensing device 100. In some implementations, the pressure-sensing devices 100 can include circular frame openings. In some implementations, the pressure-sensing devices 100 can include a rectangular frame opening. The frame opening 158 can extend through the membrane frame 136. Put another way, the frame opening 158 can extend from the bottom surface 154 of the membrane frame 136 to the top surface 152 of the membrane frame 136.

Some device electronics (e.g., electronic components and/or wires) can be disposed within the frame opening 158. For example, the pressure sensor 110 and other electronic components can be disposed within the frame opening 158 such that the pressure sensor 110 and other electronic components are disposed within the pressure chamber 108. In some implementations (e.g., FIG. 10), wires can be fed from the electronics chamber, through the frame opening 158, and into the pressure chamber 108.

The frame opening 158 can be recessed into the membrane frame 136 on the top surface 152 of the membrane frame 136. The pressure sensor 110 and/or the device electronics disposed with the recessed portion may be located such that depression of the flexible membrane 104 does not contact, or minimally contacts, the pressure sensor 110 and/or the device electronics. Instead, in this implementation, the flexible membrane 104 may come into contact with the top surface 152 of the membrane frame 136 around the recessed portion. The recessed portion may therefore serve to minimize or eliminate contact between the flexible membrane 104 and the pressure sensor 110 and/or device electronics. Although the recessed portion is illustrated as rectangular and circular, the recessed portion may have other geometries.

The portion of the frame opening 158 in which the pressure sensor 110, other electronics, and/or wires may be disposed may have a variety of different geometries. In some implementations, the frame opening 158 may define a slit (e.g., FIG. 10) through which wires or a flexible PCB (e.g., 150-4 of FIG. 10) can be disposed. In other implementations, the frame opening 158 may define a circular hole (e.g., FIG. 6) in which the pressure sensor 110 is disposed such that a portion of the pressure sensor 110 is included in the pressure chamber 108 and the remaining portion of the pressure sensor 110 is included within the circular hole, or under the bottom surface 154 of the membrane frame 136.

The pressure chamber 108 can be sealed off from the electronics chamber using a seal (referred to herein as a "frame seal"). The frame opening 158 can be sealed with a frame seal that can include an o-ring 156, although alternative types of seals may be used. In some cases, the frame opening 158 can be sealed with a compressed "face seal" or a "gland seal" design, where an o-ring or other compressible material is held in a compressed position between two rigid, air-tight surfaces. In FIG. 8A and FIG. 9, the o-ring compression is maintained by the circuit board fasteners 160 (e.g., heat-stake plastic features in FIG. 8A and screws in FIG. 9), but this compressive force could be achieved through other mechanical fastening methods such as snaps. Another technique for sealing the frame opening 158 may include using a sealant material that can flow into the opening and then chemically transition into a rigid or flexible air-tight seal. This technique may be referred to as "potting."

The membrane frame 136 defines a vent opening 162 that houses the vent components of the vent assembly 128. The vent opening 162 can extend from the pressure chamber 108 to outside of the pressure-sensing device 100. The vent assembly 128 may include components that maintain the pressure chamber 108 in a sealed state during use. A user may interact with the vent assembly 128 in order to equalize the pressure in the pressure chamber 108 to the outside pressure.

Two different vent assemblies 128-1, 128-2 are illustrated in the figures. The vent assemblies 128-1, 128-2 each include a vent shuttle 130, a vent o-ring 166, a vent spring 168, and a spring retainer 170 (e.g., a vent washer in FIG. 12 and a vent cap in FIG. 11) that maintain the pressure chamber 108 in a sealed state during use. In FIG. 12, the vent washer 170 may be snapped into place and act as a retention clip. In FIG. 11, the vent cap 170 may be fastened to the top of the membrane frame 136-1 using a heat staking process or other fastener. FIGS. 11-12 illustrate the pressure-sensing device 100 at a resting state in which a user is not using the pressure-sensing device 100 and is not interacting with the vent assembly 128 to equalize the pressure in the pressure chamber 108 and the outside. In the resting state, the vent spring 168 is slightly compressed between the spring retainer 170 and the vent shuttle 130. In this state, the vent spring 168 presses the vent shuttle 130 downwards onto the vent o-ring 166, which provides an airtight seal between the pressure chamber 108 and the environment outside of the pressure-sensing device 100. In order to equalize the pressure in the pressure chamber 108 with the outside pressure, the user may depress the portion of the vent shuttle 130 at the base surface 112 to further compress the vent spring 168 and create an opening above the vent o-ring 166. The portion of the vent shuttle 130 exposed at the base surface 112 may be sized such that the male portion of the plug for the charging port 118 or a human finger can be used to depress the vent shuttle 130 and equalize the pressure.

Referring now to the pressure-sensing device 100-1 of FIGS. 4-6, the device frame 102 includes a base portion 138-1 that may include two separate components that are attached to one another (e.g., using screws or other fasteners). The base portion 138-1 includes membrane frame supports 172-1 that support the membrane frame 136-1 above the electronics chamber. The membrane frame supports 172-1 are illustrated as flanges upon which the membrane frame 136-1 rests during use. The membrane frame supports 172-1 may provide structural support for the membrane frame 136-1 so that the membrane frame 136-1 does not substantially flex when the user sits on the pressure-sensing device 100-1. The membrane frame supports 172-1 may be attached to the membrane frame 136-1 using fasteners, such as screws (e.g., holes are illustrated for such screws in FIG. 7C). Rigidity provided by the membrane frame supports 172-1 may help minimize the distortion of the frame structure in response to pressure changes in the pressure chamber 108, which may aid in maximizing the sensitivity of the pressure-sensing device 100-1 to small pressure fluctuations because the rigidity may prevent excessive volume expansion of the pressure chamber 108 in response to externally applied pressure.

The membrane frame 136-1 can be contoured to the underlying electronic components. For example, the membrane frame 136-1 includes a raised portion 174 that is formed to contour around the underlying vibrating motor 124. The membrane frame 136-1 may include additional contours in other implementations.

The pressure-sensing device 100-1 can include one or more PCBs in the pressure chamber 108 and/or the electronics chamber. The pressure-sensing device 100-1 includes 2 PCBs 150-1, 150-2. A first PCB 150-1 includes the pressure sensor 110 and additional electronics (e.g., signal conditioning and wireless communication electronics). The second PCB 150-2 may include electronics that support operation of the USB connection (e.g., power and/or data transfer).

The first PCB 150-1 is fastened to the bottom surface 154-1 of the membrane frame 136-1 such that the pressure sensor 110 protrudes through the frame opening 158. The frame opening 158 defined by the membrane frame 136-1 includes a circular shaped hole, although other shapes are contemplated. The pressure sensor 110 is disposed within the circular hole such that the pressure sensor 110 protrudes from the circular hole but does not protrude out above the top surface 152-1 of the membrane frame 136-1.

The PCBs 150-1, 150-2 can be fastened to the membrane frame 136-1 using circuit board fasteners 160 (e.g., screws 160 illustrated in FIG. 6). Other structures that may be used to hold the PCBs 150-1, 150-2 in position may include, but are not limited to, heat stakes (described herein), snaps that may be molded into the plastic frame (e.g., the snaps may flex out of the way as the PCB is pressed past them), and adhesives (e.g., a fast-curing adhesive, such as UV-cure products).

The pressure-sensing device 100-1 includes a frame seal 156 that seals the pressure chamber 108 from the electronics chamber. In FIG. 9, the frame seal 156 may include an o-ring sandwiched between the PCB 150-1 and the bottom surface 154-1 of the membrane frame 136-1. Although an o-ring is illustrated, it is contemplated that other types of seals may be used.

FIGS. 3A-3B and FIG. 8A illustrate another example pressure-sensing device 100-2 that includes a flexible membrane 104 and a device frame 102-2. The device frame 102-2 includes a base portion 138-2 that is fabricated as a single component. The membrane frame 136-2 includes frame supports 172-2 (e.g., posts in FIG. 12) that extend outward below the bottom surface 154-2 of the membrane frame 136-2. The frame supports 172-2 fasten to the base portion 138-2 using screws that are inserted through the base portion 138-2 and threaded into the frame supports 172-2.

The frame supports 172-2 may be included within the electronics chamber when the membrane frame 136-2 is fastened to the base portion 138-2. The frame supports 172-2 may provide structural support for the membrane frame 136-2 so that the membrane frame 136-2 does not substantially flex when the user sits on the pressure-sensing device 100-2.

The base portion 138-2 includes a sidewall 144 that extends from the base surface 112-2 upward toward the attachment region 114-2 of the membrane frame 136-2. The sidewall 144 may be formed around the entire perimeter of the base portion 138-2. When the membrane frame 136-2 and the base portion 138-2 are assembled, the sidewall 144 may surround the electronics chamber including the device electronics and the frame supports 172-2. The sidewall 144 may extend from the base surface 112-2 to the attachment region 114-2 such that the electronics chamber cannot be viewed from outside of the pressure-sensing device 100-2. For example, the flexible membrane 104 may closely meet the sidewall 144 at the portion of the flexible membrane 104 that tucks under the membrane frame flange 140-2. The flexible membrane 104 may meet the sidewall 144 in what appears from the exterior of the pressure-sensing device 100-2 as a seam between the flexible membrane 104 and the sidewall 144. In some implementations, the sidewall 144 may include openings for power cable connections, data cable connections, user interface devices, and other connections.

The pressure-sensing devices 100-2, 100-3 of FIG. 8A and FIG. 10 can include one or more PCBs 150 in the pressure chamber 108 and/or the electronics chamber. In FIG. 10, the pressure-sensing device 100-3 includes two PCBs 150-4, 150-5. A first PCB 150-4 includes the pressure sensor 110 and additional electronics (e.g., signal conditioning electronics). The first PCB 150-4 may be a flexible PCB that extends from the recessed portion of the membrane frame 136-3 through an opening in the membrane frame and into the electronics chamber. A second PCB 150-5 (e.g., a rigid PCB) is included in the electronics chamber. The first and second PCBs 150-4, 150-5 can connect to one another. For example, wires or electronic traces from the two PCBs 150-4, 150-5 may connect to each other in the electronics chamber. In this implementation, the frame opening 158 may be sealed using a silicone sealant/caulking that is injected into the seams/slit and then allowed to cure into a flexible, air-tight material.

FIG. 8A illustrates an implementation of the pressure-sensing device 100-2 that includes a single PCB 150-3 that is similar to that included in the pressure-sensing device 100-1 of FIG. 6. The single PCB 150-3 may be a rigid PCB that includes the pressure sensor 110. The PCB 150-3 is fastened to the bottom surface 154-2 of the membrane frame 136-2 such that the pressure sensor 110 protrudes through the frame opening 158. In FIG. 8A, the circular shaped hole is included within the rectangular recessed portion of the frame opening 158. The pressure sensor 110 is disposed within the circular hole such that the pressure sensor 110 protrudes from the circular hole but does not protrude out of the recessed portion.

The PCB 150-3 is fastened to the membrane frame 136-2 using circuit board fasteners 160. The circuit board fasteners 160 protrude under the bottom surface 154-2 of the membrane frame 136-2 into the electronics chamber. The PCB 150-3 defines openings that receive the circuit board fasteners 160. During assembly, the circuit board fasteners 160 can be fit through the PCB openings such that the surface of the PCB 150-3 that includes the pressure sensor 110 faces the bottom surface 154-2 of the membrane frame 136-2. In FIG. 8A, the circuit board fasteners 160 can be fabricated (e.g., molded/machined/printed) from the same piece of material as the membrane frame 136-2. For example, the fasteners 160 may be "heat stakes" that hold the PCB 150-3 down against the frame seal o-ring 156. The mushroom shape at the end of the fasteners 160 may be formed by pressing down onto a cylindrical post with a heated element that softens the plastic and forces it to mushroom out. This may be accomplished in three stages: (1) applying compressive force between the PCB 150-3 and the plastic frame 136-2 (to provide pre-load force to compress the o-ring 156; (2) while still maintaining the compressive force, the heat stakes 160 are formed and allowed to cool; and (3) the compressive force is removed, thereby allowing the heat stake 160 features to be put in tension to maintain the compressive force on the o-ring 156. In other implementations, other structures may be used to hold the PCB in position other than heat stakes.

Figure 14:
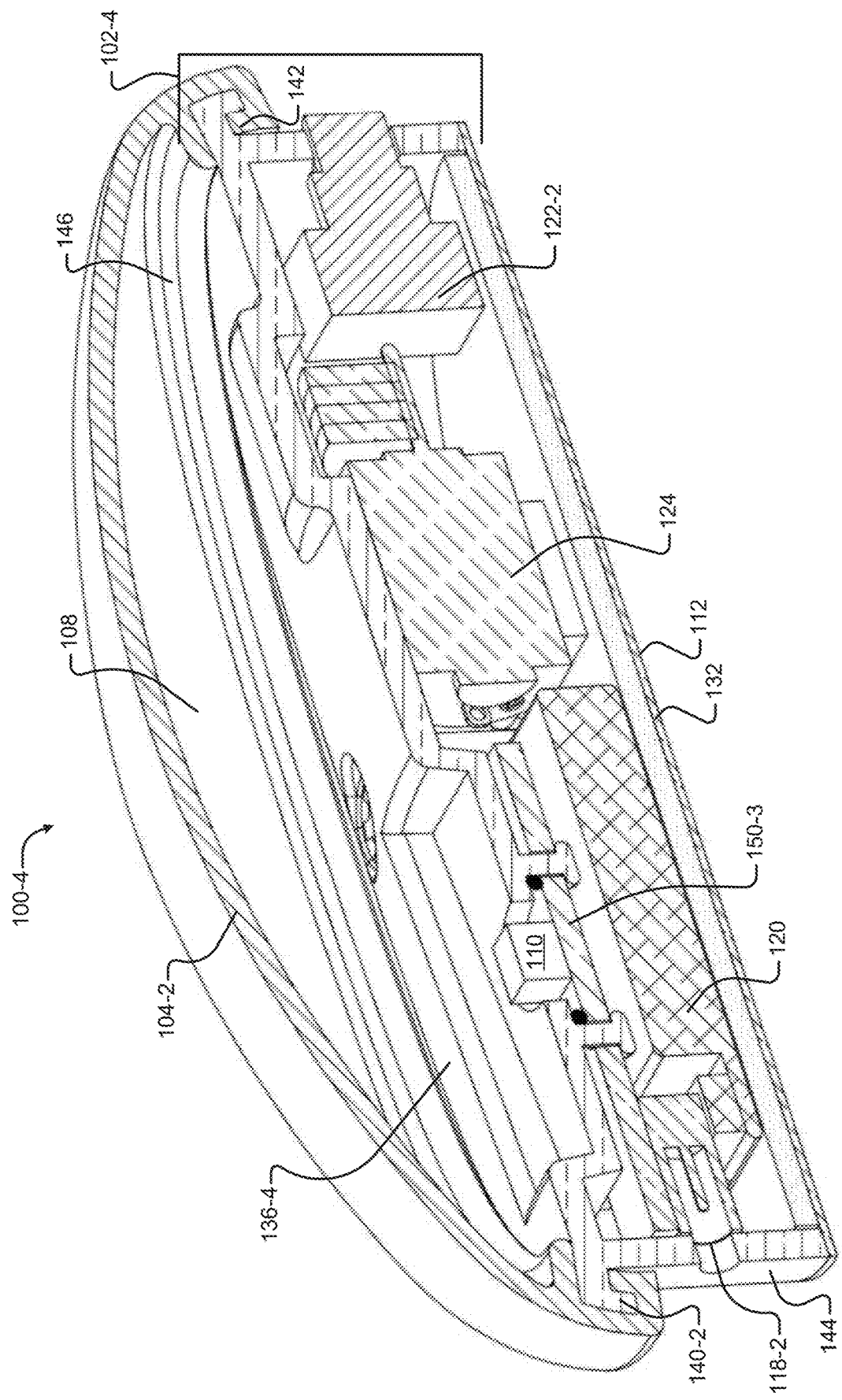

FIG. 14 illustrates an example pressure-sensing device 100-4 having a different device frame than the pressure-sensing device 100-2 of FIG. 8A. Specifically, the membrane frame 136-4 and the base portion 138-3 of the pressure-sensing device 100-4 differ from the membrane frame 136-2 and the base portion 138-2 of the pressure-sensing device 100-2.

The membrane frame 136-4 includes a sidewall portion 144 that extends downward (e.g., at approximately 90 degrees) from the bottom surface of the membrane frame 136-4. The sidewall portion 144 can extend downward near the outer edge of the membrane frame 136-4. In FIG. 12, the flange 140-2 forms the outer perimeter of the membrane frame 136-4 and the sidewall portion 144 is located inward from the flange 140-2. The sidewall portion 144 may be fabricated (e.g., molded/machined/printed) from the same piece of material as the membrane frame 136-4. Although the sidewall 144 is illustrated herein as extending perpendicular to the base surface 112, in other implementations the sidewall 144 may form an angle other than perpendicular with respect to the base surface 112.

The sidewall 144 may form the outer walls of the electronics chamber. The sidewall 144 may include one or more openings for accessing device electronics within the electronics chamber. For example, the sidewall may include openings for user interface devices (e.g., buttons), power connectors, and/or data connectors.

The base portion 138-3 of the pressure-sensing device 100-4 can be a flat piece of material that connects to the membrane frame 136-4 at the bottom edge of the sidewall 144. In some implementations, frame supports (e.g., screw bosses) may protrude from the membrane frame 136-4, which may allow the base portion 138-3 to be screwed to the membrane frame 136-4. The base surface 112 of the pressure-sensing device 100-4 may comprise a surface of the base portion 138-3 and, in some implementations, the bottom edge of the sidewall 144. The base portion 138-3 may be fabricated from the same type of material as the membrane frame 136-4 (e.g., plastic) in some implementations. In some implementations, the base portion 138-3 may be fabricated from metal in order to add weight to the pressure-sensing device 100-4. In some implementations, a base pad 132 may be added to the base surface 112 in order to prevent sliding of the pressure-sensing device 100-4 during use.

Figure 15:
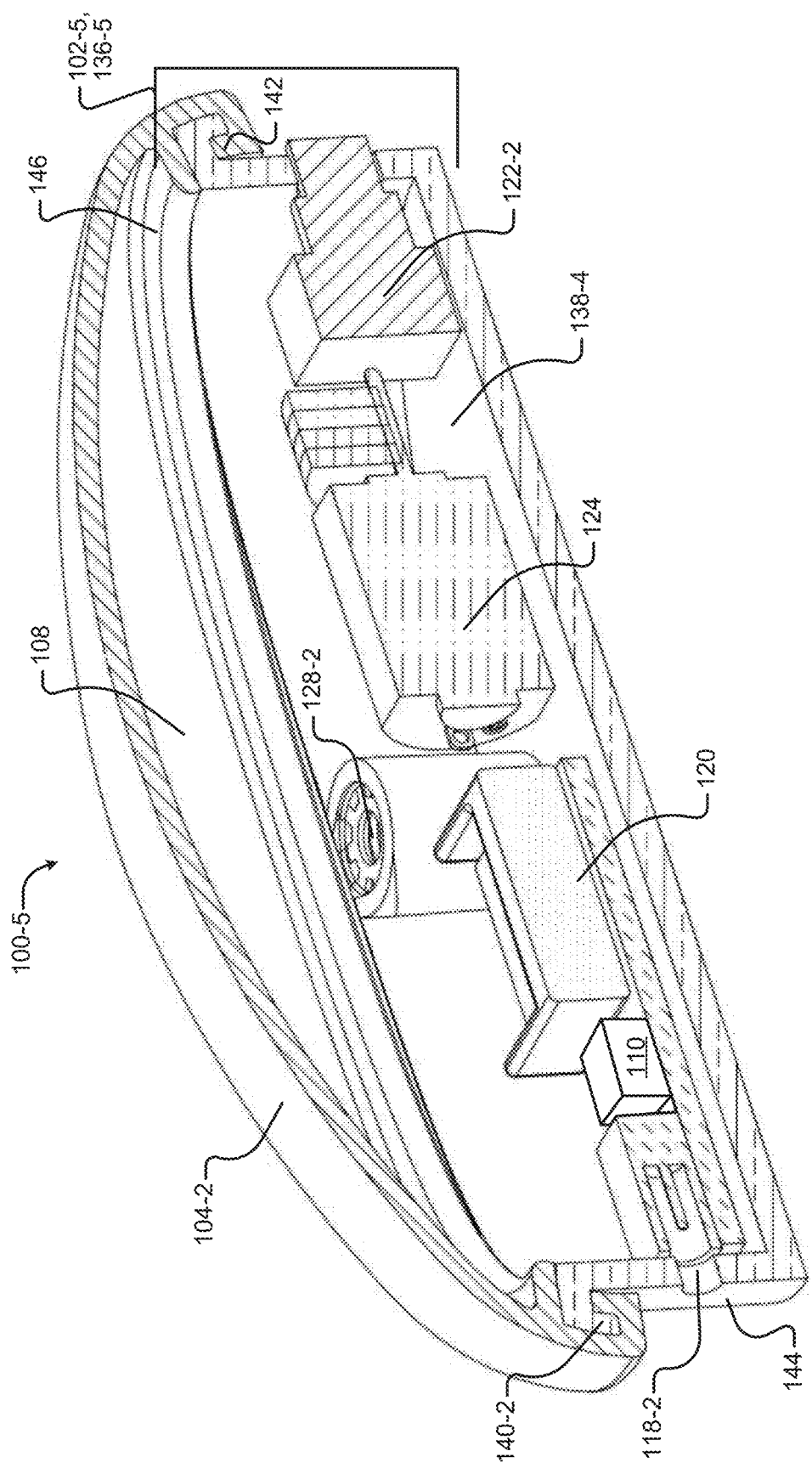

FIG. 15 illustrates another example pressure-sensing device 100-5. The device frame 102-5 is fabricated (e.g., molded/machined/printed) from a single piece of material, which is referred to as the membrane frame 136-5. The membrane frame 136-5 includes a sidewall 144 having a similar geometry to the sidewall of the pressure-sensing device 100-4 except that the sidewall 144 of FIG. 15 does not fasten to a separate base portion component. Instead, the one-piece membrane frame 136-5 forms a flattened base portion 138-4 that is continuous with the sidewall 144. The flattened base portion 138-4 of the one-piece membrane frame 136-5 includes a base surface 112 for resting the pressure-sensing device 100-5 on an external support.

Note that the pressure-sensing device 100-5 includes a single chamber that may be referred to as the pressure chamber 108. The pressure chamber 108 may include the device electronics. Accordingly, the pressure chamber 108 and the device chamber may be one and the same in the pressure-sensing device 100-5. In the pressure-sensing device 100-5, the interior of the one-piece membrane frame 136-5 and the interior of the flexible membrane 104 define the outer edges of the pressure chamber 108.

Although not illustrated in FIG. 15, the pressure-sensing device 100-5 may include the same electronic components included in the other pressure-sensing devices 100 described herein. The pressure-sensing device 100-5 may include one or more openings that extend from the pressure chamber 108 to the outside of the pressure-sensing device 100-5. One or more components in the pressure chamber 108 can be disposed within the openings such that the user can interact with the one or more components outside of the pressure-sensing device 100-5. As illustrated in FIG. 15, in some implementations, the pressure chamber 108 may include a user interface component (e.g., a user input button 122-2) that extends from within the pressure chamber 108, through an opening in the membrane frame 136-5, to the outside of the pressure-sensing device 100-5. As also illustrated in FIG. 15, in some implementations, the pressure chamber 108 may include a charging port 118-2 (e.g., a barrel plug connector) that extends from within the pressure chamber 108, through an opening in the membrane frame 136-5, to the outside of the pressure-sensing device 100-5. The membrane frame 136-5 may include seals around the various openings in order to maintain the pressure chamber 108 in an airtight state.

In some implementations, the pressure-sensing device 100-5 may include features that prevent the flexible membrane 104 from being depressed onto the device electronics included in the pressure chamber 108. For example, the pressure-sensing device 100-5 may include ribs (not illustrated) integrated into the membrane frame 136-5 that extend above the device electronics so that the flexible membrane 104 contacts the ribs instead of the tops of the device electronics. The ribs may also stiffen the membrane frame 136-5 to prevent the membrane frame 136-5 from flexing during use. Although ribs may be integrated into the membrane frame 136-5, it is contemplated that other protection/stiffening features could be included in the pressure-sensing device 100-5.

Methods for fabricating the pressure-sensing device 100 are now described. The steps for fabricating the pressure-sensing devices 100 are described at a high level, and are therefore not exhaustive. Furthermore, it is contemplated that alternative or additional fabrication steps others than those listed may be employed.

The pressure-sensing devices 100 of FIG. 6 and FIG. 8A may be fabricated according to the following steps:
1) Assembly of the pressure chamber:
   a) Test PCB(s) for functionality (e.g., battery charging, pressure sensing, Bluetooth connection, button function, LED behavior, etc.).
   b) Install vent assembly into membrane frame.
   c) Test air-tightness of vent assembly.
   d) Seal PCB with pressure sensor to membrane frame.
   e) Test air-tightness of seal between membrane frame and PCB.
   f) Seal flexible membrane to membrane frame (e.g., either adhesive or mechanical seal).
   g) Test pressure chamber for air-tightness and test pressure sensor response.
2) Assembly of device frame and then pressure-sensing device:
   a) Install device electronics and other components in device frame.
   b) Test full device function.
   c) Secure the two assemblies together (e.g., with screws or other fasteners).

The pressure-sensing device 100-3 of FIG. 10 may be fabricated according to the following steps:
1) Assembly of the pressure chamber:
   a) Test PCBs for functionality (e.g., battery charging, pressure sensing, Bluetooth connection, button function, LED behavior, etc.).
   b) Install vent assembly into membrane frame.
   c) Test air-tightness of vent assembly.
   d) Seal flexible PCB with pressure sensor to membrane frame.
   e) Test air-tightness of seal between membrane frame and flexible PCB.
   f) Solder vibrating motor to flexible PCB beneath membrane frame and secure vibrating motor to membrane frame.
   g) Seal flexible membrane to membrane frame (e.g., either adhesive or mechanical seal).
   h) Test pressure chamber for air-tightness, test pressure sensor response, and test motor response.
2) Assembly of device frame and then pressure-sensing device:
   a) Solder battery to main PCB.
   b) Install button and main PCB into base portion.
   c) Solder flexible PCB to main PCB.
   d) Connect the pressure chamber assembly to the device frame assembly.
   e) Test full device function.
   f) Secure the two assemblies together (e.g., with screws or other fasteners).

The pressure-sensing device 100-4 of FIG. 14 may be fabricated according to the following steps:
1) Test PCB for functionality (e.g., battery charging, pressure sensing, Bluetooth connection, button function, LED behavior, etc.).
2) Solder battery to PCB.
3) Install vent assembly into membrane frame.
4) Test air-tightness of vent assembly.
5) Seal PCB with pressure sensor to membrane frame.
6) Test air-tightness of seal between membrane frame and PCB.
7) Seal flexible membrane to membrane frame (e.g., either adhesive or mechanical seal).
8) Test pressure chamber for air-tightness and test pressure sensor response.
9) Install button into membrane frame.
10) Solder vibrating motor to PCB beneath membrane frame and secure vibrating motor to membrane frame.
11) Test full device function, including motor response.
12) Attach base portion.

The pressure-sensing device 100-5 of FIG. 15 may be fabricated according to the following steps:
1) Test PCBs for functionality (e.g., battery charging, pressure sensing, Bluetooth connection, button function, LED behavior, etc.).

2) Solder battery to PCB.
3) Install vent assembly into membrane frame.
4) Test air-tightness of vent assembly.
5) Install PCB, vibrating motor, and user input button.
6) Test devices (e.g., pressure sensor) for functionality (e.g., using alternative pressure source for pressure sensor because pressure chamber is not yet enclosed).
7) Seal flexible membrane to membrane frame (e.g., either adhesive or mechanical seal).
8) Test full device function, including air tightness of pressure chamber.

FIGS. 16A and 16B illustrate example implementations of pressure-sensing devices 100-1, 100-2 in a handheld form factor configured to fit into a single hand. The handheld form factor may facilitate portability. In FIG. 16A, a user is holding the pressure-sensing device 100-1 in a single hand and squeezing the flexible membrane 104 using their thumb. In FIG. 16B, a user is holding the pressure-sensing device 100-2. Although the pressure-sensing devices 100-1, 100-2 are illustrated as handheld in FIGS. 16A-16B, in other implementations, the pressure-sensing devices 100-1, 100-2 may have larger or smaller form factors (e.g., a keychain form factor).

The pressure-sensing devices illustrated in the figures can be fabricated in a variety of dimensions and weights. In some implementations, the length (e.g., the longer dimension) of the pressure-sensing device 100 may be in the range of 50-200 mm. In these implementations, the width (e.g., shorter dimension) of the pressure-sensing device 100 may be in the range of 50-150 mm. The thickness of the pressure-sensing device 100 from the base surface 112 to the top of the flexible membrane 104 may be in the range of 20-35 mm, where the flexible membrane 104 has a height (e.g., above the seating surface) of 10-20 mm. In one specific example, the pressure-sensing device 100-1 of FIG. 16A may have the following dimensions: a length of approximately 170 mm, a width of approximately 100 mm, and a height/thickness (from the top of flexible membrane 104 to the bottom of the device frame 102) of approximately 27 mm. In another specific example, the pressure-sensing device 100-2 of FIG. 16B may have the following dimensions: a length of approximately 90 mm, a width of approximately 50 mm, and a height/thickness (from the top of flexible membrane 104 to the bottom of the device frame 102) of approximately 30 mm. The dimensions of the pressure-sensing device may vary (e.g., greater or less than the pressure-sensing device illustrated in FIGS. 16A-16B). The mass of the pressure-sensing device 100 may be in the range of between 50-200 g, although it is contemplated that the pressure-sensing devices 100 may have masses outside of this range. In a specific example, the pressure-sensing devices 100-1, 100-2 of FIGS. 16A-16B may have masses of approximately 190 g and 60 g, respectively.

Figure 17:
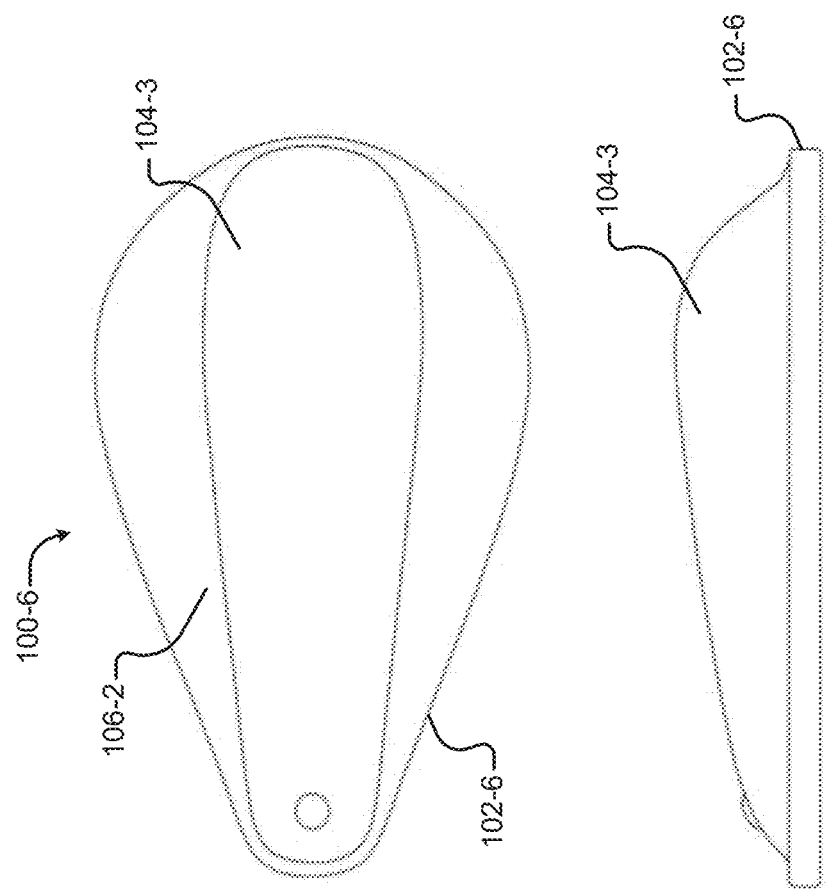
FIGS. 17-19F illustrate additional example pressure-sensing devices.

FIGS. 17-19F illustrate a variety of different example pressure-sensing devices 100 having different form factors and designs than illustrated in FIGS. 1-16B. FIG. 17 illustrates an example pressure-sensing device 100-6 having a shape that is similar to the pressure-sensing device 100-1. However, the flexible membrane 104-3 of the pressure-sensing device 100-6 extends from edge-to-edge along an axis of the pressure-sensing device 100-6.

Figure 18A:
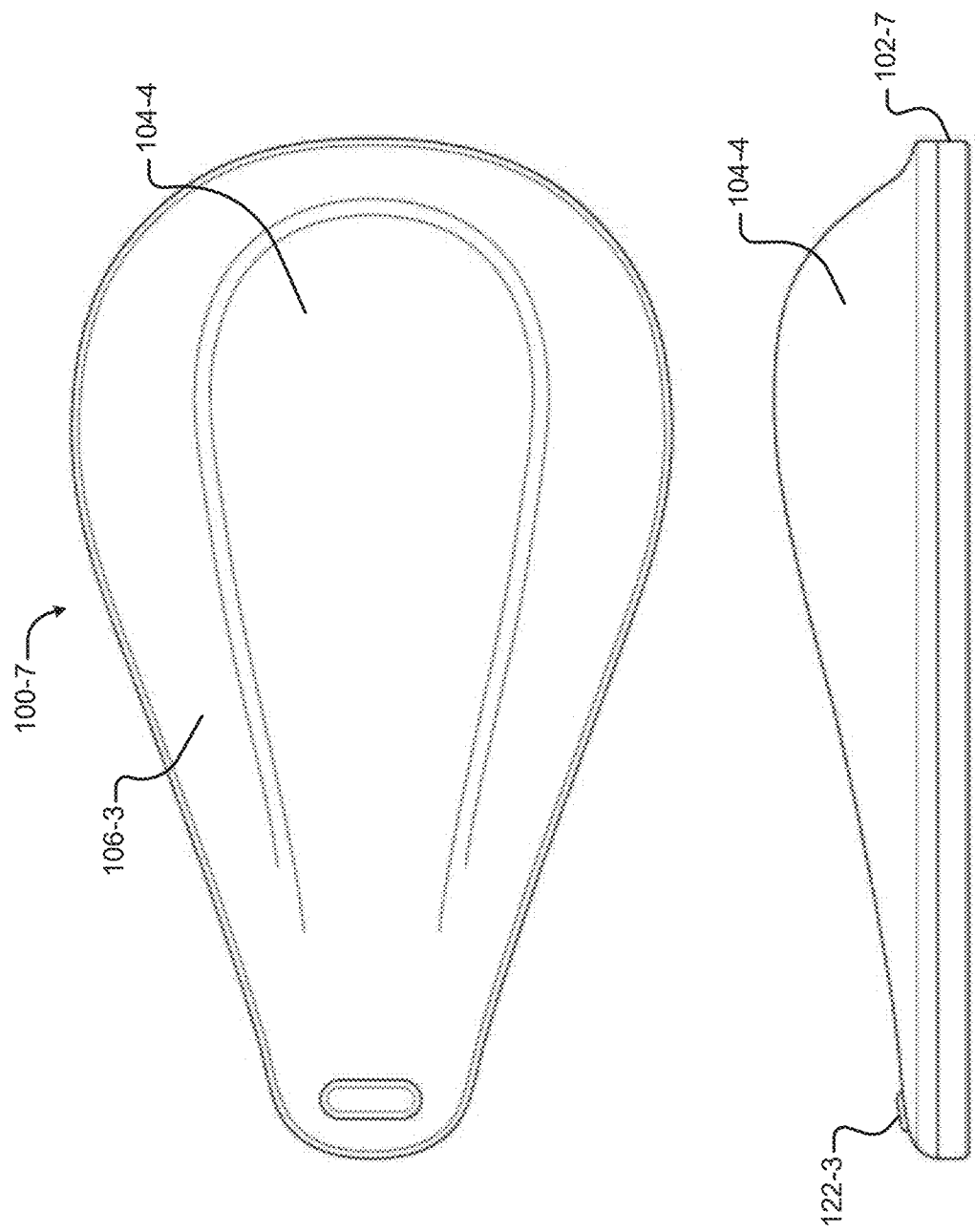
Figure 18B:
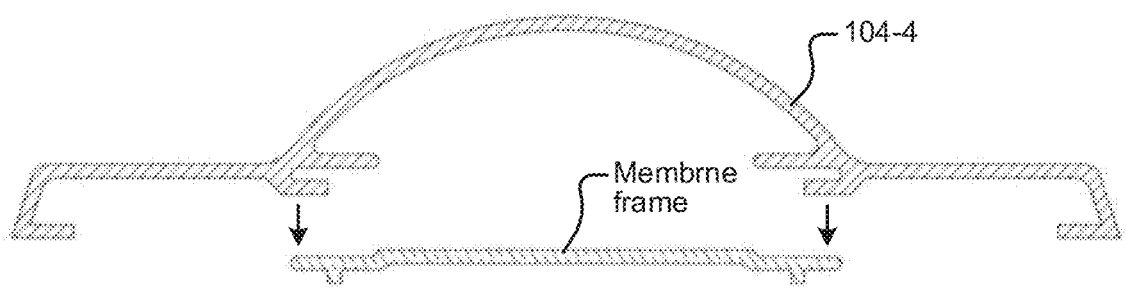
Figure 18C:
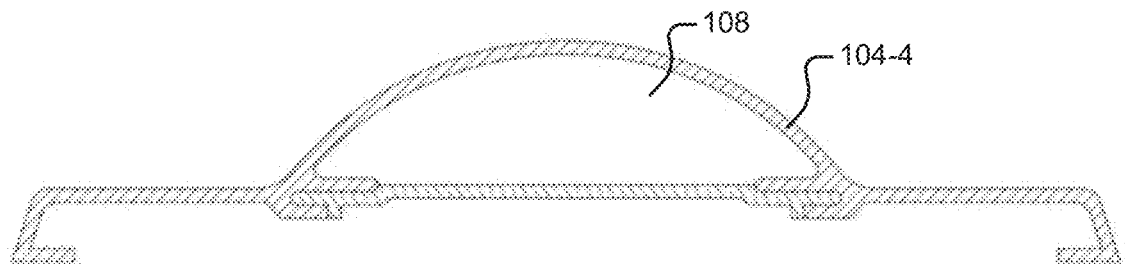
Figure 18D:
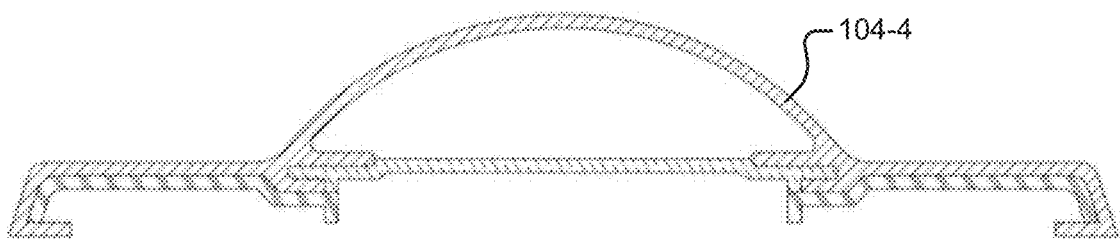
Figure 18E:
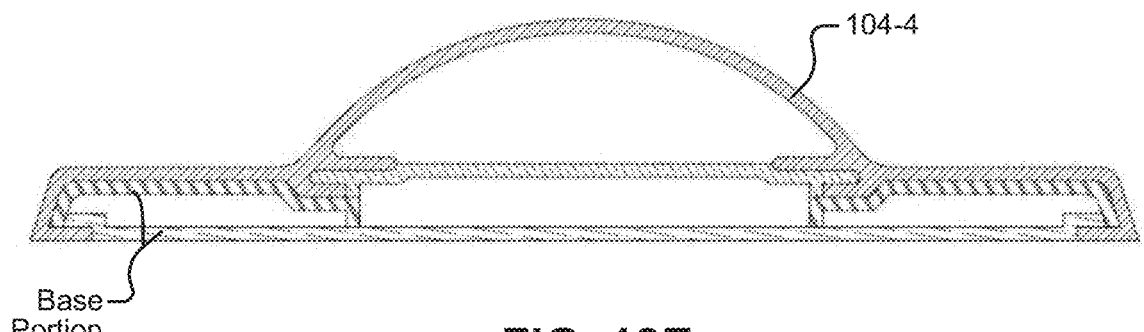

FIGS. 18A-18E illustrate an example pressure-sensing device 100-7 including a flexible membrane 104-4 that extends across the seating surface 106-3. The flexible membrane 104-4 may act as a taut cover that covers the seating surface and some of the device frame. The flexible membrane 104-4 protrudes in the center of the device frame in a manner similar to that of the pressure-sensing device 100-1. FIGS. 18B-18E illustrate how the flexible membrane 104-4 may attach to the membrane frame and base portion. In some implementations, the flexible membrane 104-4 may wrap around and under the device frame (see FIGS. 18D-18E). In other implementations, the flexible membrane 104-4 may terminate on the sidewall of the pressure-sensing device 100-7, as illustrated in FIG. 18A.

FIG. 19A illustrates an example pressure-sensing device 100-8 including rectangular device frame 102-8 having a rectangular seating surface 106-4. The flexible membrane 104-5 protrudes from the center of the device frame 102-8. The protruding pressure chamber has an elongated shape similar to that of the pressure-sensing device 100-2.

Figure 19B:
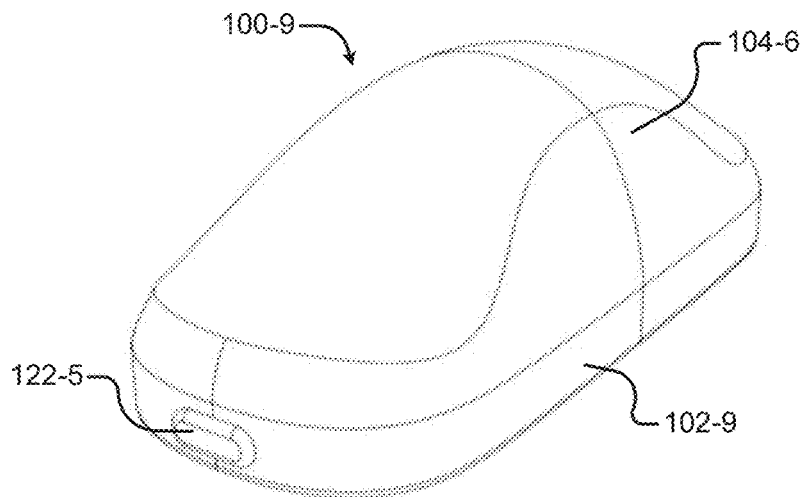
Figure 19C:
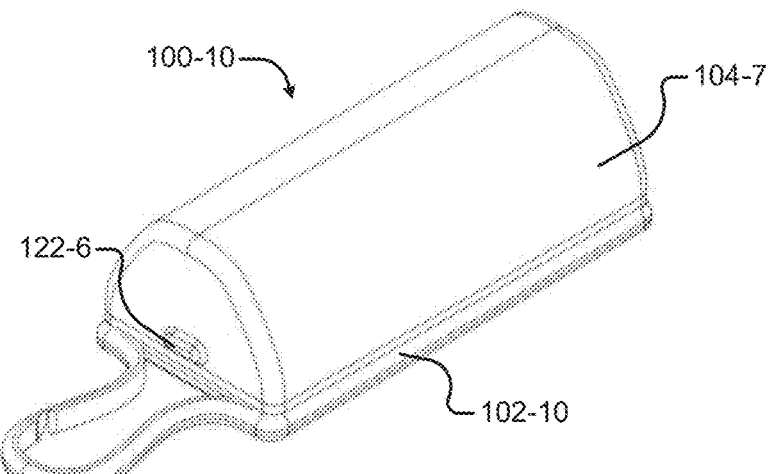

FIG. 19B illustrates a pressure-sensing device 100-9 that has a similar construction as pressure-sensing device 100-2. However, the flexible membrane 104-6 and device frame 102-9 are contoured in a different manner than the pressure-sensing device 100-2. FIG. 19C illustrates a pressure-sensing device 100-10 having a trapezoidal cross section. In addition, the device frame 102-10 of the pressure-sensing device 100-10 can be connected to a detachable carrying loop (e.g., a keychain loop or carabiner-type loop). Using the carrying loop, the user can carry the pressure-sensing device 100-10 on a keychain or other device. The carrying loop may be attached to the pressure-sensing device 100-10 in a variety of ways (e.g., via a magnetic connection or a fastener).

Figure 19D:
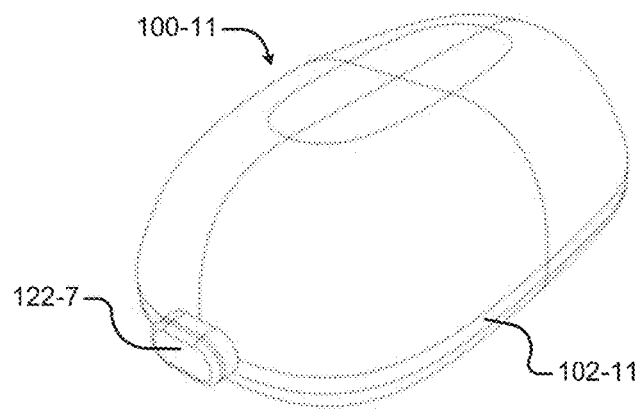
Figure 19E:
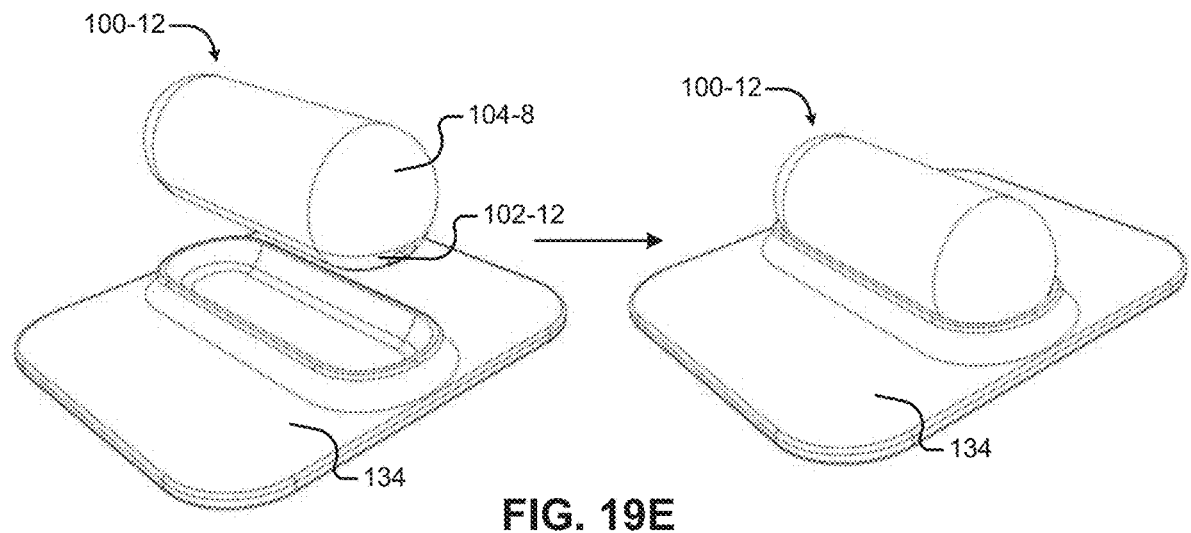

FIG. 19D illustrates a pressure-sensing device 100-11 that has a similar construction as pressure-sensing device 100-2. However, the flexible membrane and device frame 102-11 are contoured in a different manner than the pressure-sensing device 100-2. FIG. 19E illustrates an example pressure-sensing device 100-12 having a cylindrical shape (e.g., a pill capsule shape). The pressure-sensing device 100-12 includes a device frame 102-12 and a flexible membrane 104-8 that are attached to one another to form the cylindrical shape. FIG. 19E also illustrates an example external base 134 that can hold the pressure-sensing device 100-12 during exercise. The external base 134 has a generally flat structure. The middle of the external base 134 has a raised portion that is contoured to receive the pressure-sensing device 100-12 and hold the pressure-sensing device 100-12 during exercise.

Figure 19F:
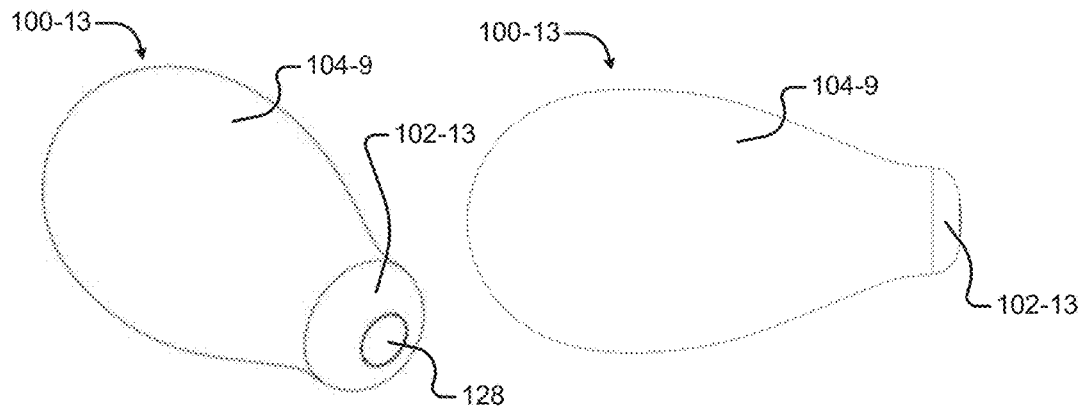

FIG. 19F illustrates a pressure-sensing device 100-13 having a bulb shape (e.g., a balloon shape) in which the flexible membrane 104-9 surrounds the device frame 102-13. In this implementation, the device frame 102-13, pressure sensor, and device electronics may be included within the bulb shaped flexible membrane 104-9. The flexible membrane 104-9 may be compressed from any direction. For example, the flexible membrane may be compressed at the tip and/or around the circumference of the bulb shaped flexible membrane 104-9 during exercise. The pressure-sensing device 100-13 may include a vent assembly 128 and/or user interface components at the exposed portion of the device frame 102-13.

FIG. 20 is a functional block diagram of an example pressure-sensing device 200. The various modules represent functionality (e.g., circuits and other components) included in the pressure-sensing device 200. Modules of the present disclosure may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits and/or other signal conditioning circuits). The modules may also include digital circuits (e.g., combinational or sequential logic circuits, memory circuits, etc.). Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein. The device electronics of the pressure-sensing devices 100 described herein are only example device electronics. As such, the types of electronic devices used to implement the device electronics may vary based on design considerations.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

The pressure-sensing device 200 includes a processing module 202, a communication module 204, a signal conditioning and A/D module 206 (hereinafter "signal conditioning module 206"), an interface module 208, and a power module 210. The pressure-sensing device 200 also includes a pressure sensor 212, one or more interface devices 214, and a battery 216. The processing module 202 communicates with the modules included in the pressure-sensing device 200. For example, the processing module 202 may transmit/receive data to/from the modules and other components of the pressure-sensing device 200.

The processing module 202 may communicate with the memory 218. The memory 218 may include computer-readable instructions that, when executed by the processing module 202, cause the processing module 202 to perform the various functions attributed to the processing module 202 herein. The memory 218 may include any volatile, non-volatile, magnetic, or electrical media, such as RAM, ROM, NVRAM, EEPROM, Flash memory, or any other digital media. In some implementations, the processing module 202 may include a microcontroller, such as a Broadcom BCM20736S that incorporates a Bluetooth radio along with rewritable program memory, I/O ports, motor control PWM channels, and A/D functionality.

The pressure sensor 212 generates a pressure signal that indicates the pressure in the pressure chamber 108 (i.e., the chamber pressure). The pressure sensor 212 can include a variety of different technologies that sense the chamber pressure. In one implementation, the pressure sensor 212 may be a microelectromechanical system (MEMs) pressure sensor. In some implementations, the pressure sensor 212 may be a piezo-resistive pressure sensor (e.g., a Silicon Microstructures Incorporated SM5420C pressure sensor) that has a continuous analog output. Alternative pressure sensors may rely on capacitive variations or other sensing schemes. In some implementations, the pressure signal may be an analog voltage that indicates the chamber pressure. In other implementations, the pressure signal may be a digital signal that indicates the chamber pressure. The digital signal may be continuously transmitted in a digital format (e.g., packets of information), or it may be sent on-demand when requested by the processing module 202 via a digital communication protocol. The chamber pressure indicated by the pressure signal may also be referred to herein as "pressure data," which may refer to a digital representation of the chamber pressure.

Although the pressure-sensing device 200 includes an electronic pressure sensor 212, in other implementations, a pressure-sensing device 200 may include different components for sensing pressure. For example, although not illustrated in the figures, in some implementations of the pressure-sensing devices 100, 200 the pressure-sensing device 100, 200 may include an element/assembly (e.g., in the membrane frame 136) that moves in response to a pressure change in the pressure chamber 108. The pressure-sensing device 100, 200 may include a displacement sensor that measures the movement of the element/assembly and determines a pressure change based on the measured movement. In some implementations, the element/assembly may include a pressure-sensing membrane between the pressure chamber 108 and the electronics chamber that flexes in response to pressure changes in the pressure chamber 108. In this implementation, the pressure-sensing device 100, 200 may include an optical sensor (the displacement sensor) that detects deflections in the pressure-sensing membrane. In other implementations, the pressure-sensing device 100, 200 may include a magnet that is forced to move in response to a change in chamber pressure. In these implementations, a magnetic sensor (the displacement sensor) may detect the change in chamber pressure based on the strength of the detected magnetic field.

The signal conditioning module 206 may include signal conditioning circuits, such as amplification circuits and/or filtering circuits that amplify and/or filter the pressure signal (e.g., the analog pressure signal). Circuit components for linear amplification of the analog signal may be selected to deliver a desired DC offset as well as output gain. By adjusting these two parameters for the desired application, it may be possible to provide maximum sensitivity and maximum range, given the available range of voltage. For example, with a voltage range of 0-3V, it may be desirable to choose the amplification such that normal user behavior leads to an output that is in the middle of the voltage range (e.g., approximately 1-2V). This may allow room for fluctuations above and below due to altitude, weather, and above/below average user ability. In addition, it may be desirable that an average user output of the amplified signal leads to a large enough usable output range from the analog-to-digital conversion stage. For example, if the A/D converter has a full scale range of 0-3000 ticks, then it may be desirable for an average user to generate a signal that results in a 0-1500 tick range (e.g., approximately 50% of the full scale). This can leave room for variability above and below this target.

The signal conditioning module 206 may also include an analog-to-digital converter (A/D) circuit in implementations where the pressure signal is an analog signal. An example A/D converter may be capable of resolving the human-scale pressure fluctuations present in the pressure-sensing device 100, 200. The resolution of an example A/D converter may be 16-bits, which may translate to approximately 1 mV (the 0-3V full scale input is mapped to 3000 ticks in the A/D output). The A/D converter may operate at a rate fast enough to be imperceptible to the human user. In practice, a sample rate of at least 20 Hz may be adequate to meet this requirement. However, many A/D converters (such as that included in the Broadcom BCM20736S system-on-a-chip) that may be used are capable of operating at a much higher frequency (e.g., approximately 100 kHz). In some implementations, the pressure sensor package may include amplification/filtering/digitizing circuits. In these implementations, the pressure sensor 110, 212 may output a digital pressure signal.

The processing module 202 receives the pressure signal output by the signal conditioning module 206. The processing module 202 may determine the chamber pressure based on the received signal. In some implementations, the processing module 202 may include an A/D converter. For example, if the processing module 202 includes a microcontroller, the microcontroller may include one or more A/D inputs that digitize analog signals.

The interface devices 214 may include user-feedback devices and/or user input devices. For example, user-feedback devices 214 may include, but are not limited to, vibration devices, lighting devices (e.g., LEDs), and a speaker. The interface module 208 can control the user-feedback devices. For example, the interface module 208 may include motor control circuits, LED control circuits, speaker control circuits, and/or other control circuits. In some implementations, the processing module 202 may control the interface devices 214 via the interface module 208. For example, the processing module 202 may generate control signals that the interface module 208 uses to control the interface devices 214. For example, the interface module 208 may include circuits that deliver power to the vibration/lighting devices, while the processing module 202 controls the delivery of power to the vibration/lighting devices. In some implementations, the pressure-sensing device 100, 200 may include combinations of LEDs, resistors, and transistors that are connected-to and driven-by I/O pins of a microcontroller (e.g., a Broadcom BCM20736S microcontroller).

Example user input devices include, but are not limited to, buttons and switches. The interface module 208 may include circuits for receiving user input signals from the user input devices. The processing module 202 may receive the user input signals from the interface module 208 and take a variety of actions based on the user input signals. For example, the processing module 202 may detect a user pressing the user input button 122 and then power up the pressure-sensing device 100, 200 (e.g., power up some currently powered down electronic devices) in response to detection of the press. As another example, the processing module 202 may detect a user pressing the input button 122 and then set the reference value (described herein) at the current chamber pressure in response to detection of the press.

In some implementations, the pressure-sensing device 100, 200 (e.g., using the interface module 208, the signal conditioning module 206, and/or the processing module 202) may generate a tangible and/or visible output based on the chamber pressure. For example, the vibration device or lights may dynamically respond to a user's contractions. In one specific example, the amount of feedback (e.g., vibration strength and/or light output) may vary according to the strength of a user's contractions (e.g., stronger contractions may cause more vibration and/or light output).

The communication module 204 can include circuits that provide wired and/or wireless communication with the user device 220. In some implementations, the communication module 204 can include wired communication circuits, such as USB communication circuits. In some implementations, the communication module 204 can include wireless communication circuits, such as Bluetooth circuits and/or WiFi circuits.

The processing module 202 can transmit/receive data to/from the user device 220 via the communication module 204. For example, the processing module 202 can transmit pressure data to the user device 220 indicating the chamber pressure. The processing module 202 can also receive data/commands from the user device 220. Example data/commands may include requests for specific information as well as commands to adjust the behavior of the pressure-sensing device 100, 200. Information requests can include status updates (e.g., charging status, battery charge level, request for download of recent exercise data, configuration settings for the feedback elements, and/or hardware gain settings). Accordingly, using the communication module 204, the pressure-sensing device 100, 200 and the user device 220 can communicate with each another. In some implementations, the processing module 202 (e.g., a microcontroller) may include circuits that provide wired/wireless communication (e.g., USB/Bluetooth).

The pressure-sensing device 100, 200 may be programmed and tested by a computing device (e.g., the user device 220 or other computing device) during manufacturing. In some implementations, the user device 220 can transfer update data to the pressure-sensing device 100, 200 to update the software/firmware of the pressure-sensing device 100, 200 after the user purchases the pressure-sensing device 100, 200.

The pressure-sensing device 100, 200 and the user device 220 may communicate with each other while the user is using the pressure-sensing device 100, 200. For example, the pressure-sensing device 100, 200 may transmit pressure data to the user device 220 that indicates the chamber pressure. The transfer of data may be done in real-time, or the pressure data may be aggregated on the pressure-sensing device 100, 200 and then sent to the user device 220 at a later time. The pressure-sensing device 100, 200 can also send status information or configuration settings back to the user device 220. These settings may include information on the specific electronic hardware and firmware being used (such as revision or version information) as well as amplification gain settings, motor configuration settings, and user behavior such as button presses, baseline pressure reference values, and inertial movement of the pressure-sensing device 100, 200. The user device 220 can use the pressure data in a variety of different ways described herein.

The pressure-sensing device 100, 200 may include a battery 120, 216 (e.g., a rechargeable or non-rechargeable battery). An example battery may include a Lithium-Ion or Lithium-Polymer type battery, with an energy capacity of 200-500 mAh, although a variety of battery options are possible. A power source (e.g., a wall adapter power plug or USB power plug) can be plugged into the charging port 118 of the pressure-sensing device 100, 200 to charge the battery 120, 216. The pressure-sensing device 100, 200 includes a power module 210 that may control charging of the battery 120, 216, regulate voltage(s) of the device electronics, regulate power output to the device electronics, and monitor the state of charge of the battery 120, 216. In some implementations, the battery 120, 216 itself may contain a Protection Circuit Module (PCM) that protects the battery 120, 216 from high current discharge, over voltage during charging, and under voltage during discharge. In some implementations, the power module 210 may include circuits configured to modulate the voltage and current into the battery 120, 216 during charging. For example, the power module 210 may include a Microchip MCP73832 charge control IC and supporting passive components. The power module 210 may also include electro-static discharge (ESD) protection.

The chamber pressure can vary due to a variety of different events. Pressure changes can be due to at least one of the following events: a user sitting on the pressure-sensing device 100, 200 (i.e., a sitting event), a user getting off of the pressure-sensing device 100, 200 (i.e., a standing event), a user shifting weight while on the pressure-sensing device 100, 200 (i.e., a shifting event), a user contracting and relaxing on the pressure-sensing device 100, 200 (i.e., a contraction event), atmospheric pressure changes due to changes in elevation/weather (i.e., atmospheric events).

The pressure-sensing device 100, 200 (e.g., the processing module 202) and/or the user device 220 can monitor the chamber pressure and identify any of the above mentioned events. Although the pressure-sensing device 100, 200 and/or the user device 220 can process the pressure data to detect the above mentioned events, the pressure-sensing device 100, 200 is described hereinafter as processing the pressure data and sensing events. For example, the processing module 202 may process the pressure data and detect the various above mentioned events.

While being used as an exercise device, the pressure-sensing device 100, 200 may attempt to identify contraction events. For example, the pressure-sensing device 100, 200 may detect the occurrence of a contraction event and/or the strength of contraction based on the pressure data. In order to do so, the pressure-sensing device 100, 200 may be configured to reject the other pressure changes (e.g., shifting events, atmospheric events, and sitting events) as contraction events.

In order to detect contraction events, the pressure-sensing device 100, 200 may be configured to detect relative changes in chamber pressure, instead of an absolute value in pressure, as the absolute chamber pressure may vary in different ways depending on the user and the atmospheric pressure. For example, weight differences in users may affect the chamber pressure differently. In one specific example, heavier users may generate a greater chamber pressure than lighter users. In another example, the manner in which a user sits on the pressure-sensing device 100, 200 may change the chamber pressure. In another example, the chamber pressure may be lower for users that use the pressure-sensing device 100, 200 at higher altitudes.

In order to monitor the relative pressure changes that may be indicative of a contraction event, the pressure-sensing device 100, 200 may define a reference value, around which a pressure change may be indicative of a user's contraction. In general, a contraction may cause an increase in chamber pressure. A contraction may then be followed by a subsequent relaxation, which may cause a decrease in chamber pressure similar to the increase caused by the contraction. The pressure-sensing device 100, 200 may identify a contraction by detecting an increase in chamber pressure above the reference value that is indicative of a contraction and/or by detecting a decrease in chamber pressure indicative of relaxation.

The pressure-sensing device 100, 200 may update the reference value over time so that the pressure-sensing device 100, 200 can detect a contraction event at any point in time the user is using the pressure-sensing device 100, 200. In general, the pressure-sensing device 100, 200 may detect a contraction event when the pressure increases above the reference value in a manner consistent with a user's contraction. The pressure-sensing device 100, 200 may modify the reference value in circumstances where the pressure change is not indicative of a contraction event. For example, the pressure-sensing device 100, 200 may modify the reference value (e.g., to a current chamber pressure) if the chamber pressure increases at a rate that is slower (e.g., an atmospheric event) or faster (e.g., a sitting/shifting/standing event) than a user's contraction. As another example, the pressure-sensing device 100, 200 may modify the reference value (e.g., to the current chamber pressure) if the chamber pressure increases or decreases to a value that is greater (or less) than could be caused by a user's expected maximum contraction/relaxation (e.g., a sitting/standing/shifting event).

In some implementations, the pressure-sensing device 100, 200 can implement a dampening in the algorithm that sets the reference value. For example, instead of setting the reference value to the exact value of the current chamber pressure, the pressure-sensing device 100, 200 may gradually transition the reference value toward the current chamber pressure in cases where the chamber pressure varies due to events other than contraction events. Implementing a dampening value may prevent setting the reference value to an inappropriately high/low level due to quick transient/ringing effects, such as a user quickly relaxing after a hard contraction.

In some implementations, the user can set the reference value, which may then be automatically updated over time, as described above. For example, the user may interact with a user input device to set the reference value. In one specific example, the user may press the user input button 122 to set the reference value to the current chamber pressure. In some implementations, the user may be provided a graphical user interface (GUI) button on the user device 220 that the user may select (e.g., touch) in order to set the reference value to the current chamber pressure. In some use cases, the user may set the reference value after the user has sat on the pressure-sensing device 100, 200 and is ready to begin exercise.

FIG. 21 is a graph that illustrates chamber pressure and the reference value over time while the user is using the pressure-sensing device 100, 200. The Y axis illustrates absolute pressure. The X axis illustrates the time during which the user uses the pressure-sensing device 100, 200. Note that the scale in the figures may not be accurately reproduced. Instead, some of the features (e.g., magnitude of the pressure changes) may be exaggerated for illustration purposes. The reference value is illustrated as the solid line. The chamber pressure is illustrated as the broken line.

At A (time T=0), the user turns on the pressure-sensing device 100, 200 (e.g., powers on the device electronics using a user input button). Initially, the reference value is set to the initial chamber pressure. At B, the user sits on the pressure-sensing device 100, 200, which causes a sharp increase in chamber pressure. At C, the user manually sets the reference value to the current chamber pressure. For example, the user may press the user input button 122 and/or a button on the GUI of the user device 220. During interval D, the pressure-sensing device 100, 200 detects three contraction events. The contraction events are indicated by the three separate pressure bumps, each including an increase in chamber pressure followed by a subsequent decrease in chamber pressure.

At E, the user adjusts their weight on the pressure-sensing device, which causes a drop in chamber pressure. The pressure-sensing device 100, 200 may adjust the reference value in response to the drop in a number of ways, depending on how the pressure-sensing device 100, 200 is configured. In one implementation, the pressure-sensing device abruptly adjusts the reference value to the chamber pressure (at F) after the chamber pressure has been at the lower value for a period of time. In another implementation, the pressure-sensing device adjusts the reference value gradually over time according to a dampening value, as described above.

During interval G, the pressure-sensing device 100, 200 detects three contraction events. At K, the chamber pressure rapidly increases and then falls back down to the previous level. The abrupt change in pressure at K (e.g., caused by a user weight shift and/or strong contraction) may not cause a shift in reference value because the change was too abrupt (e.g., faster than the reference value may follow). Put another way, the abrupt change was ignored for the purposes of adjustment of the reference value. At H, the chamber pressure dip represents a transient dip (e.g., an undershoot) in chamber pressure. The pressure-sensing device 100, 200 may not adjust the reference value due to the short duration of the dip.

The chamber pressure gradually increases and decreases between I and J. The pressure-sensing device 100, 200 gradually adjusts the reference value to match the chamber pressure over time during the increase/decrease in chamber pressure.

The user device 220 (e.g., a smartphone, tablet, laptop, or other computing device) can execute an application that interfaces with the pressure-sensing device 100, 200. The user device 220 may download and install the application after the user purchases the pressure-sensing device 100, 200. The application can provide a variety of different features for interfacing with the pressure-sensing device 100, 200. For example, the application may generate a GUI that allows the user to control the pressure-sensing device 100, 200 and receive feedback from the pressure-sensing device 100, 200. Providing control/feedback to the user allows the user to become immersed in the exercise routines and track their immediate and past progress.

The application may provide a variety of features. The GUI may include GUI elements (e.g., buttons) that allow the user to set the reference value. The GUI may display the chamber pressure (e.g., as a number and/or a curve over time), count the number of contractions, show a history of contractions, and show statistics for a current or past exercise routine. The GUI may also provide interactive feedback prompting the user to contract. For example, the GUI may prompt the user to contract a certain number of times. As another example, the GUI may prompt the user to contract at a certain intensity. In some cases, the application may prompt/remind the user to exercise.

The application may store any of the exercise data described herein on the user device 220 and/or a remote server (not shown) so that a user can review historic data to track their progress. In some implementations, the application may provide a platform for sharing exercise information/history with friends or health professionals.

Figure 22A:
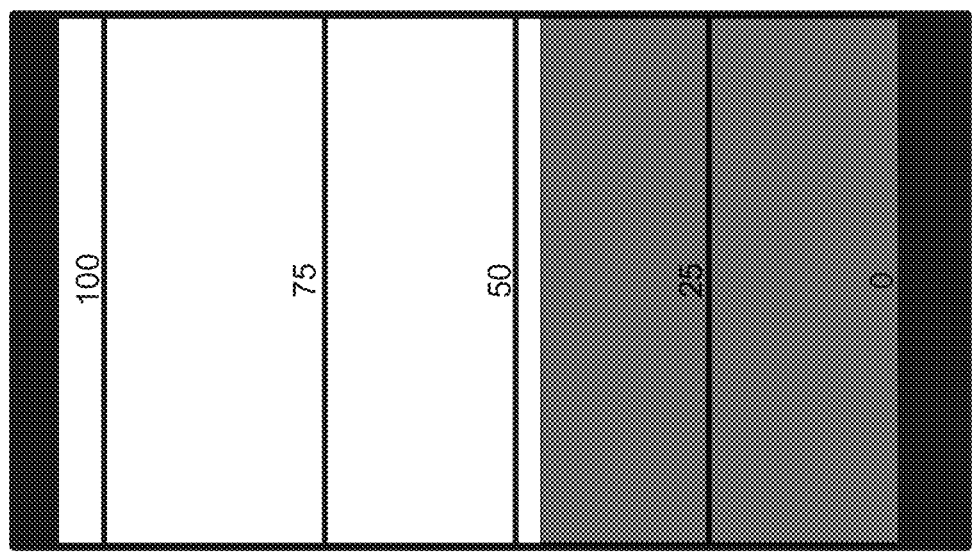
FIGS. 22A-22D illustrate example graphical user interfaces generated on a user computing device for interacting with the pressure-sensing device.
Figure 22B:
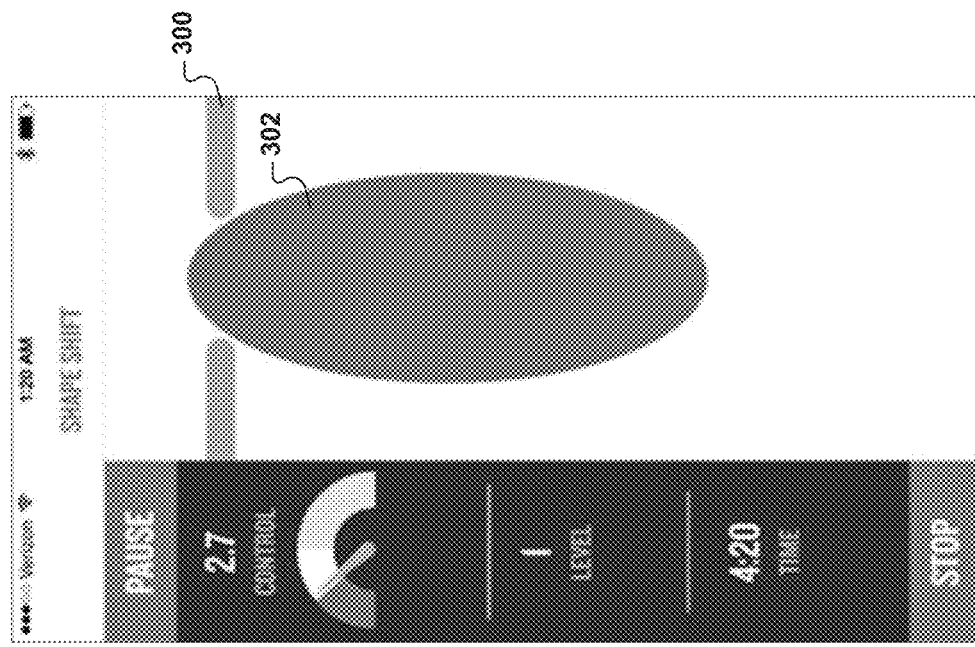

FIGS. 22A-22D illustrate example GUIs that may be provided by the application (e.g., exercise routines and games) on the user device display. The example exercise and game applications illustrated in FIGS. 22A-22D may provide a user with a way to track their progress and be entertained, thereby promoting the user to use and re-engage with the pressure-sensing device 100. FIG. 22A illustrates a GUI that indicates contraction strength (e.g., from 0-100). The application may track the strength of contractions over time and log the user's exercise session. FIG. 22B illustrates an example GUI that prompts the user to contract in a controlled manner. The strength of the user's contractions controls the width of the opening between the horizontal bars 300 (e.g., strong contractions open the bars 300 wider). The oval shape 302 moves from the bottom of the screen toward the top of the screen. The goal of the user is to contract in such a way that the horizontal bars 300 open sufficiently to let the oval shape 302 pass between the horizontal bars 300. Such an exercise routine may help the user develop the exercised muscles.

Figure 22D:
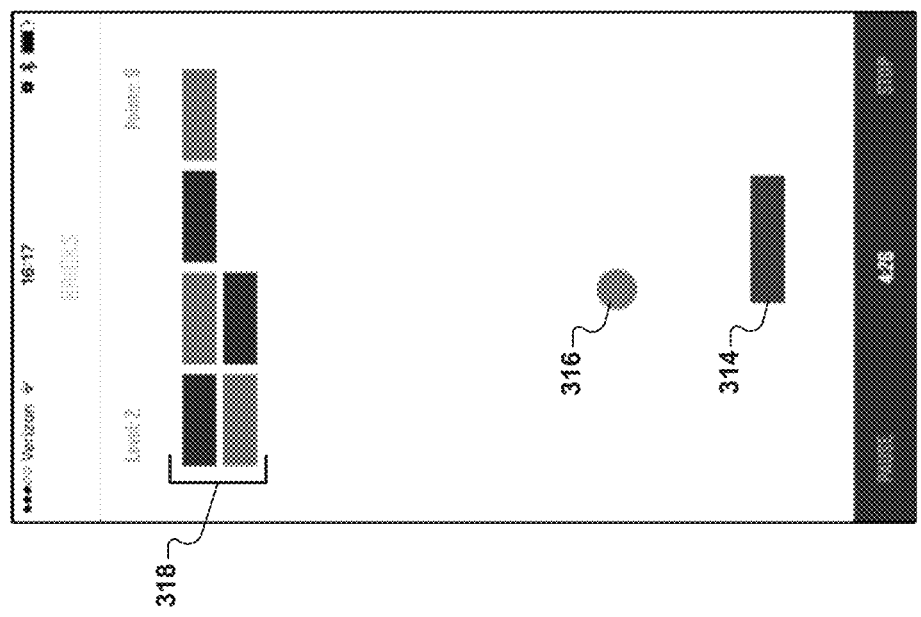
Figure 22C:
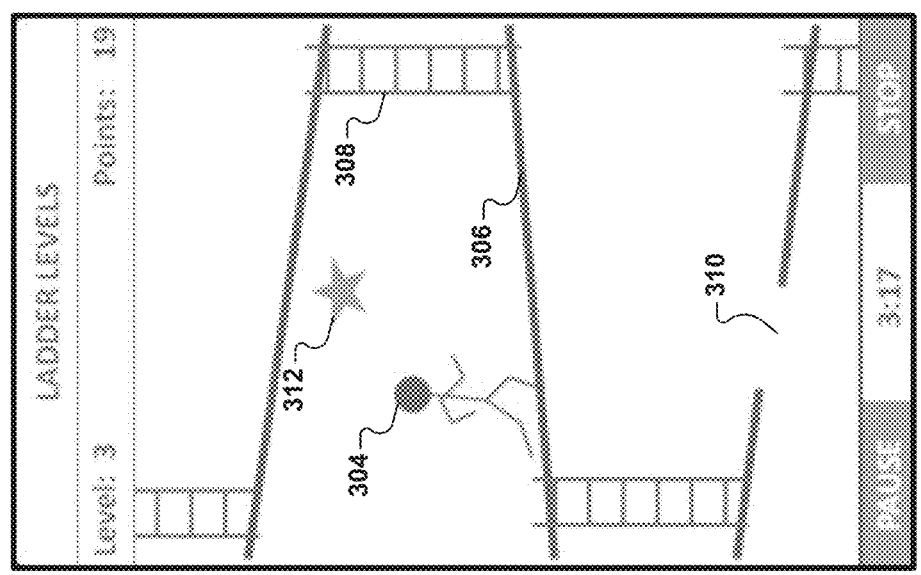

FIG. 22C illustrates an example game which may execute on the user device 220. In FIG. 22C, the user can control a game character 304 by contracting. For example, a contraction event may cause the game character 304 to perform an action in response to the contraction event. In the game illustrated in FIG. 22C, the character 304 may independently walk along the floor 306 and climb the ladders 308 of the level. The user may contract (i.e., cause a contraction event) to cause the character 304 to jump. Specifically, the user may contract to cause the character 304 to jump the gap 310 in the floor 306 and/or acquire the star 312 in order to accumulate points in the game. In similar games (not illustrated), the game may prompt the user to contract to perform other game character actions, such as ducking and changing speeds.

FIG. 22D illustrates an example game which may execute on the user device 220. In FIG. 22D, the user can control a paddle 314 in a horizontal direction by contracting. For example, a contraction event may cause the paddle 314 to approach the ball 316 that moves vertically/horizontally on the screen. In the game of FIG. 22D, the user may perform a contraction above a threshold strength to move the paddle 314 in a direction towards the ball 316. If the user is successful in performing the contraction, then the ball 316 may bounce off of the paddle 314 and be directed to the blocks 318 at the top of the screen. The ball 316 may then destroy one or more blocks 318 and bounce back towards the bottom of the screen, prompting the user to contract in order to move the paddle 314 back towards the ball 316. The user may accumulate points for destroying the blocks 318.

The application on the user device 220 may also process data (e.g., pressure data) received from the pressure-sensing device 100, 200. The user device 220 may perform processing on the received data to detect contraction events and reject other events. Example processing that may occur on the user device 220 may include, but is not limited to: filtering of the pressure data to detect muscle contractions, counting of the number of contractions, measurement of the relative strength and muscle endurance during an exercises session, and analysis of how closely a user is following a guided exercise routine.

As described above, the pressure-sensing device 100, 200 may transmit pressure data to the user device 220 while the user is using the pressure-sensing device 100, 200 (e.g., in real-time). In addition to the pressure data, or as an alternative to the pressure data, the pressure-sensing device 100, 200 may be configured to transmit analyzed pressure data. For example, the pressure-sensing device 100, 200 may transmit data to the user device 220 including discrete event data, such as discrete contraction events, sitting events, shifting events, or standing events. The data may include any of the values described herein, including, but not limited to, the strength of a contraction event, the time the contraction event occurred, the duration of the contraction event, the total number of contraction events, and/or the time other events (e.g., sitting/shifting/standing events) occurred. In a specific example, the pressure-sensing device 100, 200 may transmit data related to a series of contraction events, which may indicate when the contractions occurred, how strong each contraction was, and/or the duration of the contractions. In some implementations, the pressure-sensing device 100, 200 can be configured to transmit such data to the user device 220 while the user is using the pressure-sensing device 100, 200 (e.g., in real-time). In other implementations, a user may use the pressure-sensing device 100, 200 while the pressure-sensing device 100, 200 is not in communication with the user device 220. In these implementations, the data may be stored in the memory 218 of the pressure-sensing device 100, 200 and then be transferred to the user device 220 at a later time. For example, the pressure-sensing device 100, 200 may transmit the data in response to establishing a communication connection with the user device 220 or in response to a request for the data from the user device 220. In this manner, the user can use the pressure-sensing device 100, 200 without an established connection to the user device 220 and then view their data at a later time when a connection between the pressure-sensing device 100, 200 is established.

When performing pelvic floor muscle contractions while seated on the pressure-sensing device 100, 200, it may be desirable for the user to maintain good posture and focus on squeezing and lifting the pelvic floor muscles. User movements other than pelvic floor contractions (e.g., shifting of body weight or other movements) may be undesirable when performing pelvic floor muscle contractions, as such movements may not benefit the pelvic floor exercises. Accordingly, when pelvic floor exercises are done properly, the user and/or the pressure-sensing device 100, 200 may remain generally in the same position and may not move significantly.

When the user shifts his or her body weight on top of the pressure-sensing device 100, 200, the user movement may impart measurable movements in the pressure-sensing device 100, 200 (e.g., movements in the device frame 102). For example, the user may impart measurable accelerations (linear or rotational) on the pressure-sensing device 100, 200 (e.g., the device frame 102). When these user movements occur, there may be corresponding changes in the chamber pressure. When trying to distinguish actual contraction events from other pressure data in the raw stream of pressure data, it may be helpful to reject/ignore pressure changes that are occurring because of user movements other than contraction events.

In some implementations, the device electronics can include user movement sensors (not illustrated) that output user movement data that may be used by the device electronics (e.g., the processing module 202) to analyze the pressure data. The user movement sensors can be used to assist the device electronics in determining whether the changes in chamber pressure are due to a pelvic floor muscle contraction (e.g., a contraction event) or caused by other user motion (e.g., user shifting/sitting/standing). For example, if the pressure-sensing device 100, 200 includes user movement sensors, the device electronics may monitor movements of the pressure-sensing device 100, 200 independently from the pressure changes occurring within the pressure chamber. This monitoring may allow software/hardware executing on the pressure-sensing device 100, 200 and/or a user device 220 to ignore and/or filter out chamber pressure fluctuations occurring in the pressure chamber that may not be due contraction events in the pelvic floor.

Example user movement sensors may include any type of sensor that can detect movement of the pressure-sensing device 100, 200 (e.g., movement of the device frame 102). For example, user movement sensors may include accelerometers, gyroscopes, magnetometers, force sensors, or other inertial sensing technologies. User movement sensors may also include one or more microphones that detect noise due to a user shifting on top of the pressure-sensing device 100, 200. The user movement sensors may be attached internally or externally to the device frame 102. For example, the user movement sensors may be included in the electronics chamber, pressure chamber 108, within the material of the device frame 102, and/or attached externally to the device frame 102. In one specific example, one or more force sensors may be attached to the base surface 112 (e.g., as feet pads) or on the seating surface. In this example, the force sensors may detect an amount of force being asserted on the device frame 102 by the user's shift in weight.

The device electronics may determine the amount of user movement based on analysis of the user movement data. Determination of the amount of user movement based on user movement data may be sensor dependent. In some implementations, the device electronics may attempt to determine whether the user movement data indicates that a threshold amount of user movement is present. A threshold amount of user movement may refer to a scenario in which the amount of user movement may indicate that the pressure data may not reliably indicate whether a contraction event is occurring. In these cases, when the user movement sensors indicate that user movement is less than a threshold value, the pressure data may be used in a more reliable manner to identify contraction events. In one specific example in which the user movement sensor is an accelerometer, the device electronics may determine that an acceleration value greater than a threshold value may indicate that greater than a threshold amount of user movement is present. In another specific example in which the user movement sensor is a microphone, the device electronics may determine that a noise level greater than a threshold value may indicate that greater than a threshold amount of user movement is present.

The device electronics may use the user movement data generated by one or more user movement sensors to identify and reject some changes in chamber pressure, such as contraction events, shifting events, sitting events, and/or standing events. In some implementations, the device electronics may ignore pressure data that occurs contemporaneously with user movement data indicating greater than a threshold amount of user movement in order to prevent the device electronics from mischaracterizing pressure data as contraction events when the changes in chamber pressure are due to other events (e.g., shifting events). In these implementations, the device electronics may use pressure data to detect contraction events during times when the user movement data indicates less than a threshold amount of user movement (e.g., during times when user movement may be less likely to be affecting the chamber pressure).

Although the device electronics may ignore pressure data during times when user movement may be affecting the pressure data, in some implementations the device electronics may use the user movement data to filter out pressure changes resulting from user movement and extract contraction events from the filtered data. For example, the device electronics may filter out large swings in chamber pressure if the swing in chamber pressure occurs along with a detected user movement. In this example, the device electronics may analyze the filtered chamber pressure data to more reliably detect contraction events.

Although the pressure-sensing devices 100 described herein may be used for exercising, the pressure-sensing devices 100 may be used to monitor other activities. For example, the pressure-sensing devices 100 (or similarly constructed devices) may be used to monitor a user's posture. In one implementation, a pressure-sensing device can rest on a user's seat (e.g., chair, cushion, or other seating device) and monitor pressure changes to detect a user's posture. The pressure-sensing device can notify the user when the user's posture may be incorrect (e.g., using vibration, sound, or via a user device GUI). In these implementations, once the user sits on the pressure-sensing device (posture monitoring device) and sets a baseline pressure reference value, the pressure-sensing device can detect weight shifts of the user (shifting events) based on changes in the chamber pressure. For example, leaning forward in a seated position may cause weight to shift onto the pressure-sensing device, thereby causing the chamber pressure to increase. Likewise, shifting of weight backwards, via lowering and rolling the hips backwards, may cause a decrease in the measured chamber pressure (e.g., beneath the perineum). In this manner, the pressure-sensing device can act as a comfortable seat cushion that monitors posture and weight balance/distribution and may notify the user of posture information/feedback.

Various examples have been described. These and other examples are within the scope of the following claims.

What is claimed is:

1. A pressure-sensing device comprising:
   a device frame comprising:
      a base surface configured to rest on an external supporting structure that is separate from the pressure-sensing device; and
      a frame attachment region located opposite to the base surface such that the frame attachment region is raised from the external supporting structure when the base surface is resting on the external supporting structure;
   a flexible membrane including a membrane attachment region attached to the frame attachment region, wherein the flexible membrane protrudes above the device frame and is configured to conform to a user's perineum region when the user is seated on the flexible membrane, and wherein the device frame and the flexible membrane at least partially enclose a pressure chamber including an air mass between the device frame and the flexible membrane;
   a pressure sensor at least partially included within the pressure chamber and in contact with the air mass, the pressure sensor configured to generate a pressure signal indicating air pressure of the air mass in the pressure chamber; and
   device electronics configured to:
      determine the air pressure in the pressure chamber based on the pressure signal;
      determine a pressure reference value based on the determined air pressure in the pressure chamber; and
      detect a muscle contraction event based on a change in the determined air pressure in the pressure chamber relative to the pressure reference value.

2. The pressure-sensing device of claim 1, wherein the device electronics are configured to detect the muscle contraction event based on at least one of a magnitude of change in the determined air pressure and a rate of change of the determined air pressure.

3. The pressure-sensing device of claim 1, wherein the device electronics are configured to detect the muscle contraction event based on a duration of time associated with the muscle contraction event.

4. The pressure-sensing device of claim 1, wherein, after the detected muscle contraction event, the device electronics are configured to determine a modified pressure reference value in response to changes in the determined air pressure.

5. The pressure-sensing device of claim 4, wherein the muscle contraction event is a first muscle contraction event, and wherein the device electronics are configured to detect additional muscle contraction events based on changes in the determined air pressure in the pressure chamber relative to the modified pressure reference value.

6. The pressure-sensing device of claim 5, wherein the device electronics include a communication module configured to communicate with a user computing device using at least one of wired communication and wireless communication, and wherein the device electronics are configured to notify the user computing device of the first muscle contraction event and the additional muscle contraction events.

7. The pressure-sensing device of claim 4, wherein the device electronics are configured to determine the modified pressure reference value in response to changes in the determined air pressure that are indicative of events other than a user muscle contraction, and wherein the events include at least one of the user shifting weight, the user sitting down onto the pressure-sensing device, the user standing up off of the pressure-sensing device, and atmospheric pressure changes.

8. The pressure-sensing device of claim 7, wherein the device electronics are configured to:
   identify at least one of a shifting event, a sitting event, and a standing event, wherein the shifting event indicates that the user is shifting weight on the pressure-sensing device, wherein the standing event indicates that the user is standing up off of the pressure-sensing device, and wherein the sitting event indicates that the user is sitting down onto the pressure-sensing device;
   communicate with a user computing device using at least one of wired communication and wireless communication; and
   notify the user computing device of at least one of the shifting event, the sitting event, and the standing event.

9. The pressure-sensing device of claim 1, wherein the device electronics include a user movement sensor that indicates an amount of movement associated with the user sitting on the pressure-sensing device other than movement caused by muscle contractions in the user's perineum region, and wherein the device electronics are configured to detect the muscle contraction event based on the amount of movement indicated by the user movement sensor and the determined air pressure in the pressure chamber.

10. The pressure-sensing device of claim 1, wherein the device electronics include a user-feedback device configured to generate feedback to the user in response to detection of the muscle contraction event.

11. A system comprising:
    a pressure-sensing device comprising:
       a device frame comprising a base surface and a frame attachment region, wherein the base surface is configured to rest on an external supporting structure that is separate from the pressure-sensing device, and wherein the frame attachment region is located opposite to the base surface such that the frame attachment region is raised from the external supporting structure when the base surface is resting on the external supporting structure;
       a flexible membrane including a membrane attachment region attached to the frame attachment region, wherein the flexible membrane protrudes above the device frame and is configured to conform to a user's perineum region when the user is seated on the flexible membrane, and wherein the device frame and the flexible membrane at least partially enclose a pressure chamber including an air mass between the device frame and the flexible membrane;

a pressure sensor at least partially included within the pressure chamber and in contact with the air mass, the pressure sensor configured to generate a pressure signal indicating air pressure of the air mass in the pressure chamber; and device electronics configured to:

determine the air pressure in the pressure chamber based on the pressure signal; and transmit pressure data to a user computing device indicating the determined air pressure; and a non-transitory computer-readable medium comprising computer-executable instructions configured to cause the user computing device to:

determine a pressure reference value based on the determined air pressure in the pressure chamber; and detect a muscle contraction event based on a change in the determined air pressure in the pressure chamber relative to the pressure reference value.

12. The system of claim 11, wherein the computer-executable instructions are configured to cause the user computing device to indicate the muscle contraction event in a graphical user interface.

13. The system of claim 11, wherein the computer-executable instructions are configured to cause the user computing device to detect the muscle contraction event based on at least one of a magnitude of change in the determined air pressure and a rate of change of the determined air pressure.

14. The system of claim 11, wherein the computer-executable instructions are configured to cause the user computing device to detect the muscle contraction event based on a duration of time associated with the muscle contraction event.

15. The system of claim 11, wherein, after the detected muscle contraction event, the computer-executable instructions are configured to cause the user computing device to determine a modified pressure reference value in response to changes in the determined air pressure.

16. The system of claim 15, wherein the muscle contraction event is a first muscle contraction event, and wherein the computer-executable instructions are configured to cause the user computing device to detect additional muscle contraction events based on changes in the determined air pressure in the pressure chamber relative to the modified pressure reference value.

17. The system of claim 16, wherein the computer-executable instructions are configured to cause the user computing device to generate a graphical user interface that indicates at least one of the determined air pressure, a contraction count, and a history of contraction events including the first muscle contraction event and the additional muscle contraction events.

18. The system of claim 15, wherein the computer-executable instructions are configured to cause the user computing device to determine the modified pressure reference value in response to changes in the determined air pressure that are indicative of events other than a user muscle contraction, and wherein the events include at least one of the user shifting weight, the user sitting down onto the pressure-sensing device, the user standing up off of the pressure-sensing device, and atmospheric pressure changes.

19. The system of claim 18, wherein the computer-executable instructions are configured to cause the user computing device to identify at least one of a shifting event, a sitting event, and a standing event, wherein the shifting event indicates that the user is shifting weight on the pressure-sensing device, wherein the standing event indicates that the user is standing up off of the pressure-sensing device, and wherein the sitting event indicates that the user is sitting down onto the pressure-sensing device.

20. The system of claim 11, wherein the device electronics include a user movement sensor that indicates an amount of movement associated with the user sitting on the pressure-sensing device other than movement caused by muscle contractions in the user's perineum region, wherein the device electronics are configured to transmit data to the user computing device that indicates the amount of movement associated with the user, and wherein the computer-executable instructions are configured to cause the user computing device to detect the muscle contraction event based on the amount of movement associated with the user and the determined air pressure in the pressure chamber.

21. The system of claim 11, wherein the device electronics include a user-feedback device configured to generate feedback to the user, and wherein, in response to detection of the muscle contraction event at the user computing device, the computer-executable instructions are configured to send a command to the device electronics that cause the user-feedback device to generate feedback.

* * * * *